(12) United States Patent
Riss

(10) Patent No.: US 7,037,664 B2
(45) Date of Patent: May 2, 2006

(54) APOPTOSIS MARKER ANTIBODIES AND METHODS OF USE

(75) Inventor: Terry Riss, Oregon, WI (US)

(73) Assignee: Promega Corporation, Madison, WI (US)

( * ) Notice: Subject to any disclaimer, the term of this patent is extended or adjusted under 35 U.S.C. 154(b) by 517 days.

(21) Appl. No.: 10/011,321

(22) Filed: Dec. 3, 2001

(65) Prior Publication Data

US 2002/0102268 A1   Aug. 1, 2002

Related U.S. Application Data

(62) Division of application No. 09/445,615, filed as application No. PCT/US99/22262 on Sep. 24, 1999, now Pat. No. 6,350,452.

(60) Provisional application No. 60/101,920, filed on Sep. 24, 1998.

(51) Int. Cl.
*C12Q 1/70* (2006.01)
*G01N 33/53* (2006.01)

(52) U.S. Cl. .................. 435/7.1; 435/5; 436/500

(58) Field of Classification Search .............. 435/5, 435/7.1; 436/500
See application file for complete search history.

(56) References Cited

U.S. PATENT DOCUMENTS

| | | | |
|---|---|---|---|
| 4,196,265 A | 4/1980 | Koprowski et al. | |
| 4,474,892 A | 10/1984 | Murad et al. | |
| 4,554,101 A | 11/1985 | Hopp | |
| 4,916,070 A | 4/1990 | Matsueda et al. | |
| 4,927,916 A | 5/1990 | Matsueda et al. | |
| 4,975,369 A | 12/1990 | Beavers et al. | |
| 5,192,660 A | 3/1993 | Reed-Gitomer | |
| 5,225,539 A | 7/1993 | Winter | |
| 5,500,349 A | 3/1996 | Esnouf | |
| 5,536,639 A | 7/1996 | Siman et al. | |
| 5,567,595 A | 10/1996 | Kok | |
| 5,629,197 A | 5/1997 | Ring et al. | |
| 5,736,348 A | 4/1998 | Goldenberg et al. | |
| 5,744,319 A | 4/1998 | Niles et al. | |
| 6,048,703 A * | 4/2000 | Siman et al. | 435/7.1 |

FOREIGN PATENT DOCUMENTS

| | | |
|---|---|---|
| WO | WO98/21590 | 5/1998 |
| WO | WO 98/52297 | 11/1998 |
| WO | WO 99/16789 | 4/1999 |
| WO | WO00/23804 | 4/2000 |
| WO | WO 00/63250 | 10/2000 |

OTHER PUBLICATIONS

Lederman et al. (Molecular Immunology 28: 1171-1181, 1991).*
Li et al. (PNAS 77: 3211-3214, 1980).*
Ngo et al.; in The Protein Folding Problem and Tertiary Structure Prediction, 1994, Merz et al., (ed.), Birkhauser, Boston, MA, p 433 and 492-495.).*
Bayne, EK, et al., "Use of an Antibody Against the Matrix Metalloproteinase-Generated Aggrecan Neoepitope Fvdipen-COOH to Access the Effects of Stromelysin in a Rabbit Model of Cartilage Degradation", *Arthritis and Rheumatism*, 38(10): 1400-1409 (1995).
Duriez, P and Girish, MS, "Cleavage of poly(ADP-ribose) polymerase: a sensitive parameter to study cell death", *Biochemistry and Cell Biology*, 75(4): 337-349 (1997).
Fosang, AJ, et al., "Aggrecan Is Degraded by Matrix Metalloproteinases in Human Arthritis", *Journal Clinical Investigation*, 98(10): 2292-2299 (1996).
An, B. et al., *Cancer Res*. 56: 438-442, 1996.
Broncolini, C. et al., *EMBO J*. 14: 5179-5190, 1995.
Brown, S.B. et al., *Biochem. J*. 323: 233-237, 1997.
Caulin et al., *J. Cell. Biol*., 138(6):1379-94, 1997.
Campbell, Labortory Techniques in Biochemistry and Molecular Biology, vol. 13: Monoclonal Antibody Technology, ed. by Alisa M. Campbell (Pub. by Elsevier, Amsterdam, 1984), Table of Contents and pp. 66-85 (Chapter 3) "*Monoclonal Antibody Technology, Laboratory Techniques in Biochemistry and Molecular Biology*," Burden and Von Knippenberg, Eds., Elsevier, Amsterdam, 13:66-85, 1984.
Cardone et al., *Cell*, 90(2):315-23, 1997.
Casciola-Rosen, L.A. et al., *J. Biol. Chem*, 269: 30757-30760, 1994.

(Continued)

*Primary Examiner*—S. Huff
*Assistant Examiner*—C. Yaen
(74) *Attorney, Agent, or Firm*—Michael Best & Friedrich LLP

(57) ABSTRACT

Disclosed are antibodies that specifically recognize the new amino terminus of a protein cleaved by a protease during apoptosis. Methods of using and making the antibodies are also provided. The antibodies are particularly useful in methods of detecting apoptosis and testing candidate compounds for enhancing or inhibiting apoptosis.

17 Claims, 3 Drawing Sheets

OTHER PUBLICATIONS

Casciola-Rosen, L.A. et al., *J. Exp.Med.* 183: 1957-1964, 1996.
Casciola-Rosen, L.A. et al., *J. Exp. Med.* 182: 1625-1634, 1995.
Casiano, C.A. et al., *J. Exp. Med.* 184: 765-770, 1996.
Chen, L. et al., *Proc. Am. Assoc. Cancer Res.* A-25, 1996.
Chen, Wei-dong et al., *Oncogene* 14: 1243-1248, 1997.
Chen, Z. et al., *Cancer Res.* 56: 5224-5229, 1996.
Cohen, G.M. *Biochem. J.* 326, 1-16, 1997.
Crouch, D.H. et al., *Oncogene* 12: 2689-2696, 1996.
Cryns, V.L. et al., *J. Biol. Chem.* 271: 31277-31282, 1996.
Day, *Advanced Immunochemistry*, 2nd edition (Pub. by Wiley-Liss, New York, NY, 1990) Table of Contents 295-350 (Ch.7).
Duan et al., *J. Biol. Chem.*, 271:1621-1625, 1996.
Emoto, Y. et al., *EMBO J.* 14: 6148-6156, 1995.
Fornstedt, *FMEBS Lett.*, 177:195-199, 1984.
Gatti R. et al., *J. Histochem. Cytochem.*, 46(8):895-900, 1998.
Gefter M. et al., *Somatic Cell Genet.*, 3(2):231-236, 1977.
Ghayur, T. et al., *J. Exp. Med.* 184: 2399-2404, 1996.
*Monoclonal Antibodies: Principles and Practice*, by James W. Goding, 2nd edition, (Academic Press, Orlando, FL, 1986). Table of Contents pp. 59-103. (Ch. 3).
Goldberg, Y.P. et al., *Nat. Genet.* 13: 442-449, 1996.
*Antibodies: A Laboratory Manual*, by Harlow, E. et al., (Pub. by Cold Spring Harbor Labortory) Cold Spring Harbor, NY, 1988. Table of Contents.
Hsu, Hsin-Ling. et al., *J. Cell Sci.*, 109-277-288, 1996.
Jänicke et al, *EMBO J.*, 15(24):6969-6978, 1996.
Kaufmann et al., *Cancer Research*, 53:3976-3985, 1993.
Kayalar et al., *Proc. Natl. Acad. Sci.* USA, 93:2234-2238, Mar. 1996.
Köhler, A. et al., *Eur. J. Immunol.*, 6:511-519, 1976.
Köhler, A. et al., *Nature*, 256:495-497, Aug. 7, 1975.
Kyte V. et al., *J. Mol. Biol.*, 157:105-132, 1982.
Lazebnik, Y.A. et al., *Nature* 371: 346-347, 1994.
Lazebnik, Y.A. et al., *Pro. Natl. Acad. Sci. U.S.A.* 92: 9042-9046, 1995.
Le Romancer, M. et al., *J. Cell Sci.* 109: 3121-3127, 1996.
Liu, X. et al., *Cell* 89: 175-184, 1997.
Martin, S. et al., *J. Biol. Chem.* 270: 6425-6428, 1995.
Mashima, T. et al., *Biochem. Biophys. Res. Commun.* 217: 1185-1192, 1995.
Mashima, T. et al., *Oncogene* 14: 1007-1012, 1997.
Na, S. et al., *J. Biol. Chem.* 271: 11209-11213, 1996.
Nicholson and Thornberry, *TIBS*, 22(8):299-306, 1997.
Nicholson et al., *Nature*, 376:37-42, 1995.
Nicholson, *Nature Biotech.*, 14:297-301, 1996.
Oliver, F.J. et al. *J. Biol. Chem.* 273, 33533-33539, 1998.
Orth, K. et al., *J. Biol. Chem.* 271: 16443-16446, 1996.
Pepper et al., *Leuk. Res.*, 22(5):439-444, 1998.
Rao, L. et al., *J. Cell Biol.* 135: 1441-1455, 1996.
Sallmann et al., *Biochem. Cell Biol.*, 75:451-456, 1997.
Schlegel et al., *J. Biol. Chem.*, 271:1841-1844, 1996.
Song, Q. et al., *Biochem: Biophys. Res. Commun.* 233: 343-348, 1997.
Song, Q. et al., *EMBO J*, 15: 3238-3246, 1996.
Song, Q. et al., *Proc. Natl. Acad. Sci. U.S.A.* 94: 157-162, 1997.
Takahashi, A. et al., *Proc. Natl. Acad. Sci. U.S.A.* 93: 8395-8400, 1996.
Tan, X. et al., *J. Biol. Chem.* 272: 9613-9616, 1997.
Teraoka, H. et al., *FEBS Lett.* 393: 1-6, 1996.
Tewari, M. et al., *Cell* 81, 801-809, 1995.
Ubeda, M. and Habener, J.F., *J Biol Chem*, 272(31):19562-19568, 1997.
Vanags, D.M. et al., *J. Biol. Chem.* 271: 31075-31085, 1996.
Villa et al., *TIBS*, 22:388-393, 1997.
Wang, X. et al, *J. Biol. Chem.* 270: 18044-18050, 1995.
Wang, X. et al., *EMBO J.* 15: 1012-1020, 1996.
Waterhouse, N. et al., *J. Biol. Chem.* 271: 29335-29341, 1996.
Yang et al., *American Journal of Pathology*, 152(2):379-389, 1998.
Zhang et al., *The Journal of Immunology*, 157:3980-3987, 1996.
Armstrong, Robert C. et al., "Fas-induced Activation of the Cell Death-related Protease CPP32 Is Inhibited by Bcl-2 and by ICE Family Protease Inhibitors", *J Biol Chem* 271(28) 16850-16855 (Jul. 12, 1996).
Kikuchi, Hidehiko et al., "Antibodies specific for proteolyzed forms of protein kinase C α", *Biochimica et Biophysica Acta* 1269:253-259, 1995.
Küpper, Jan-Heiner et al. "Detection of poly(ADP-ribose) polymerase and its reaction product poly(ADP-ribose by immunocytochemistry", *Histochemical Journal* 28:391-395, 1996.
Lamarre, Daniel et al. "Production and characterization of monoclonal antibodies specific for the functional domains of poly(ADP-ribose) polymerase", *Biochem. Cell Biol.* 64:-368-376, 1986.
Lamarre, Daniel et al. "Structural and functional analysis of poly(ADP ribose) polymerase: an immunological study", *Biochimica et Biophysica Acta* 950:147-160, 1998.
Kikuchi, Hidehiko et al., "Activation and possible involvement of calpain, a calcium-activated cysteine protease, in down-regulation of apoptosis of human monoblast U937 cells", *Death and Differentiation*, vol. 2, 195-199 (Jul. 1995).

\* cited by examiner

GVDEVAK
(SEQ ID NO: 2)

FIG. 1

Amino Acid 196 to Amino Acid 244 of PARP (SEQ ID NO: 5)

KKQLPGVKSEGKRKGDEVD|GVDEVAKKSKKEKDKDSKLEKALKAQNDL

Caspase Recognition Site | New Amino Terminus

GVDEVAK = First Seven Amino Acids (SEQ ID NO:2)

APOPTOSIS MARKER ANTIBODIES AND METHODS OF USE

CROSS-REFERENCE TO RELATED APPLICATIONS

This application is a divisional of U.S. patent application Ser. No. 09/445,615, filed Dec. 8, 1999 now U.S. Pat. No. 6,350,452 which is a filing under 35 U.S.C. 371 of International Application No. PCT/US99/22262, filed Sep. 24, 1999 which claims priority to U.S. Provisional Patent Application Ser. No. 60/101,920, filed Sep. 24, 1998.

FIELD OF THE INVENTION

The present invention relates generally to the field of detecting and quantifying apoptosis. More particularly, the present invention relates to antibodies to the newly formed amino terminus resulting from cleavage of proteins during the process of apoptosis and to the use of such antibodies in detecting apoptosis in cells undergoing apoptosis or in cells that have undergone apoptosis.

BACKGROUND OF THE INVENTION

Most eukaryotic cells have the ability to self-destruct by activation of an intrinsic cellular suicide program referred to as programmed cell death or apoptosis The process of apoptosis involves a cascade of cytoplasmic and nuclear events that result in a series of morphological changes, and eventually cause the demise of the cell. Apoptosis is characterized by distinct biochemical and morphological changes exhibited by cells undergoing programmed cell death, including DNA fragmentation, plasma membrane blebbing, and cell volume shrinkage. At the molecular level, activation of one or more aspartate-specific, cysteine proteases (caspases) is proposed to be the critical signal required to carry out apoptotic cell death (Yang et al., *American Journal of Pathology*, 152(2):379–389, 1998).

The caspases, also known as ICE (IL-1 β-converting enzyme)-like proteases, can be divided into three subclasses: ICE/CED3 family, CPP32/Yama family and the Ich/Nedd2 family (Duan et al., *J. Biol. Chem.*, 271:1621–1625, 1996). All family members share a high level of amino acid sequence homology with ICE, and contain a conserved QACRG pentapeptide in which the cysteine participates in catalysis (Nicholson, *Nature Biotech.*, 14:297–301, 1996). Furthermore, all of these proteases are reported to require an aspartic acid residue at the substrate P1 position (Jänicke et al, *The EMBO J.*, 15(24):6969–6978, 1996).

CPP32 (Caspase 3) has been identified as one of the proteases that cleaves poly(ADP-ribose) polymerase (PARP) (Schlegel et al., *J. Biol. Chem.*, 271:1841–1844, 1996; Nicholson et al., *Nature*, 376:37–42, 1995). PARP is one of the enzymes associated with DNA repair. Cleavage of the approximately 116 kilodaltons ("kd") PARP protein into fragments of about 89 kd and about 27 kd has been reported to contribute to the DNA fragmentation that is characteristic of apoptosis (Kayalar et al., *Proc. Natl. Acad. Sci. USA*, 93:2234–2238, 1996). Therefore, the identification of the about 89 kd or the about 27 kd fragments resulting from the cleavage of PARP within a cell is an indication that the cell is undergoing or has undergone apoptosis.

Proteins consist of macromolecules of amino acids linked by peptide bonds, to form polypeptide chains. Each amino acid in the chain consists of a carbon atom to which are attached four different groups (—R, —H, —$NH_2$, and —$CO_2H$), wherein the identity of R varies from one amino acid to another. The peptide bond links each amino acid to the next amino acid in the chain through a covalent bond formed between the —$CO_2H$ group of one amino acid and the —$NH_2$ group of the next amino acid, with $H_2O$ a byproduct of the reaction. Every polypeptide chain has two terminal amino acid residues, one at each end of the chain. The end of the chain with a —$CO_2H$ group which has not been linked to another amino acid is referred to as the "carboxy terminus" or "C-terminus". The end of the chain with a —$NH_2$ group which has not been linked to another amino acid is referred to as an "amino terminus" or "N-terminus". When an enzyme such as caspase cleaves PARP, it breaks a peptide bond in a polypeptide chain of the protein, creating one fragment with a new carboxy terminus and another fragment with a new amino terminus.

One reference, WO 98/21590, describes methods of detecting apoptosis by using antibodies that bind to the amino acids at the newly created carboxy termini of polypeptides generated by the cleavage of proteins by the caspase family of proteases. Because caspases cleave immediately carboxy-terminal of a characteristic four amino acid recognition site, the newly created carboxy terminus of a caspase cleaved protein consists of the last amino acid of the recognition site. WO 98/21590 describes the production of antibodies following immunization of rabbits with a polypeptide comprising a caspase recognition site (GDEVD) at its carboxy terminus. Although the antibodies of WO 98/21590 appear to recognize a cleaved fragment of PARP, these antibodies were cross-reactive with other proteins as well. This cross-reactivity is likely to result in inaccurate determinations of apoptosis in cells or cellular lysates.

In another attempt to produce antibodies that are specific to apoptotic fragments of PARP, Sallmann et al., *Biochem. Cell Biol.*, 75:451–456, (1997) immunized rabbits with synthetic polypeptides corresponding to the newly created carboxy terminus and amino terminus of PARP that are formed following cleavage of PARP by a caspase. Although the polyclonal antibodies produced by Sallmann et al. were able to distinguish between the two (carboxy terminal and amino terminal) apoptotic fragments of PARP, the antibodies were not able to distinguish between the cleaved fragment and uncleaved PARP. Therefore, the antibodies produced by Sallmann et al. are not specific to epitopes produced in apoptotic cells because they are immunoreactive with the uncleaved PARP present in non-apoptotic cells.

Therefore, there is a need for antibodies that are specifically able to distinguish apoptotic events in cells. These antibodies will enable more accurate results in methods for detecting apoptosis. Because apoptosis, or the inability of cells to undergo apoptosis, is associated with a number of disorders and diseases including cancer, neurodegeneration, autoimmunity, heart disease and others (reviewed in Hetts, *JAMA*, 279(4):300–307, 1998), improved methods of detecting apoptosis will provide a better understanding of these diseases and will be useful in screening potential therapeutic agents that may induce or prevent apoptosis.

BRIEF SUMMARY OF THE INVENTION

The present invention seeks to overcome limitations in the prior art by providing methods and compositions related to antibodies that recognize specific epitopes that are indicators of apoptosis. Antibodies were produced that are specific to a new epitope (neoepitope) formed in apoptotic cells. The neoepitope is a product of cleavage of a protein at a specific cleavage site by a protease during apoptosis.

The present invention involves the use of antibodies raised against a neoepitope which comprises a polypeptide sequence which is homologous to only one end of one of the fragments of a protein cleaved during apoptosis. Every protein consists of a chain of amino acids. Each amino acid covalently linked to the next amino acid in the chain through a peptide bond. A peptide bond links the amine residue of one amino acid with the carboxyl residue of the next amino acid in the chain. The resulting chain has an unattached amine residue at one end, and an unattached carboxy residue at the other end. When the protein is cleaved, and the chain of amino acids broken at that point, two fragments of the protein are formed, one with a new carboxy terminus, and the other with a new terminal amine. In the present invention, the neoepitope comprises the new amino terminus at the beginning of the carboxy terminal fragment.

By immunizing animals with a polypeptide comprising a sequence of the amino acids of the newly formed amino terminus of a fragment of a protein formed by cleavage of the protein during apoptosis, antibodies were isolated that recognized the cleaved form of the protein but failed to recognize the uncleaved form. This result is surprising because attempts by others to produce specific antibodies to a new amino terminus of PARP formed after cleavage by a caspase failed because the antibodies were still immunoreactive with the uncleaved protein (Sallmann et al., *Biochem. Cell Ciol.*, 75:451–456, 1997). Furthermore, the isolated antibodies of the present invention show particular utility in methods of detecting apoptosis.

The present invention includes compositions comprising an isolated antibody that is immunoreactive with a neoepitope produced in a cell undergoing apoptosis. As used herein, the term immunoreactive means that the antibody is capable of binding the antigen with an affinity that is indicative of an immune reaction to the antigen. Such affinities are well known to those of skill in the art and include affinities of $10^5$ to $10^{14}$ $M^{-1}$. Methods of determining the affinity of an antibody composition are described in Day, *Advanced Immunochemistry*, ($2^{nd}$ edition) Wiley-Liss, New York, N.Y. (1990).

Although binding the neoepitope is an important aspect of the present invention, it is also important that the antibody fails to bind the uncleaved protein. This ability to distinguish between the cleaved and uncleaved form of a protein gives the antibody its novel specificity to detect apoptotic cells, as the neoepitope is at a detectable level in apoptotic cells but below a detectable level in non-apoptotic cells.

The antibody may be a polyclonal or monoclonal antibody and recognizes the new amino terminus of poly(ADP-ribose) polymerase (PARP) formed by cleavage of the protein by a caspase. A polypeptide comprising the amino acid sequence of FIG. 1 (SEQ ID NO:2), when injected into a rabbit, was able to cause production of antibodies that bound specifically to the cleaved form of PARP while failing to bind the uncleaved form.

Although the methods of the present invention may be employed with a number of different proteases, the inventor has found that targets of the caspase family of proteases are particularly useful. The caspase family of proteases include ICE (caspase 1), caspase 3, caspase 7, and caspase 8, and are reviewed in Nicholson, et al., *TIBS*, 22(8):299–306 (1997) and Villa et al., *TIBS*, 22:388–393 (1997). In preferred embodiments, the neoepitope is the new amino terminus of a protein cleaved by caspase 7 or caspase 3.

An antibody of the present invention may be immunoreactive with an epitope in apoptotic cells from a number of species including chicken, bovine, murine, feline, canine, rat, equine, opine, and primate species including human. In preferred embodiments, the antibody is immunoreactive with an epitope in apoptotic cells of a mammal, preferably human.

The apoptotic cell may be a cell of essentially any type known to be capable of the process of apoptotis including heart, lung, skeletal muscle, neuronal, liver, kidney, pancreas, epithelial, or blood cell. In preferred embodiments, the blood cell is a leukemia cell such as HL-60.

The antibodies of the present invention may be used in methods of detecting apoptosis in a cell or group of cells. The methods disclosed herein allow the determination of apoptosis in a biological sample comprising an individual cell or a group of cells. As used herein a group of cells may be any collection of more than one cell such as a blood sample, tissue sample, biopsy, or tissue culture. A biological sample to be screened can be a biological fluid such as extracellular or intracellular fluid or a cell or tissue extract or homogenate. A biological sample can also be an isolated cell (e.g., in culture) or a collection of cells such as in a tissue sample or histology sample. A tissue sample can be suspended in a liquid medium or fixed onto a solid support such as a microscope slide.

In some embodiments, the methods of detecting apoptosis in a cell or group of cells comprise obtaining a protein sample from the cell or group of cells, contacting the protein sample with an antibody which is immunoreactive with a neoepitope in apoptotic cells, and screening the cell or group of cells to detect any of the antibody bound to the neoepitope. Detecting the antibody bound to the neoepitope in the sample is indicative of apoptosis in the cell or group of cells, whereas failing to detect the antibody bound to the neoepitope is indicative of lack of apoptosis in a cell or group of cells. Such methods include immunoassays such as Western blots, Enzyme Linked Immunosorbent Assay ("ELISA"), cell-based ELISA, filter-binding ELISA, inhibition ELISA, sandwich ELISA, immunostaining, immunoprecipitations, slot or dot blots, radioimmunoassays, scintillation proximity assays, Ouchterlony analysis, and fluorescent immunoassays. Some of the above methods require the cells to be lysed or processed to isolate proteins therefrom prior to the detection step.

Other methods of the present invention for detecting apoptosis in cells do not require the step of acquiring a protein sample or lysate, but rather detect apoptosis in the cells or tissues themselves. Such methods include immunohistochemistry, immunocytochemistry, and flow cytometry.

In some embodiments, the antibody of the present invention further comprises a label. A label is a molecule or substance that is attached to the antibody that facilitates detection of the presence of the antibody. Labels are well known to those of skill in the art and include, but are not limited to, haptens such as biotin or nitro-iodo-phenyl, radioactive isotopes such as $^{125}I$, $^{3}H$, $^{14}C$, $^{32}P$, or $^{35}S$, enzymes such as alkaline phosphatase, horseradish peroxidase, β-galactosidase, or luciferase, and fluorescent or luminescent molecules, such as fluorescein, rhodamine, phycoerythrin, Texas red, green flourescent protein or derivatives thereof.

Antibodies of the present invention comprising labels are particularly useful in methods of detecting apoptosis in a cell, group of cells, cell sample, or sample of a group of cells. In other embodiments, the presence of an antibody of the present invention is detected by the use of a secondary antibody comprising a label.

Another embodiment of the present invention is a method of producing an antibody immunoreactive with a neoepitope produced in a cell undergoing apoptosis. This method comprises the steps of: (a) obtaining a polypeptide comprising an amino acid sequence corresponding with the amino terminus produced by cleavage of a protein by a protease during apoptosis; and (b) administering the polypeptide to an animal under conditions suitable to provoke an immune response thereby producing antibodies to the polypeptide. In preferred embodiments of this last method, antibodies obtained by such a method are removed from the animal, or in the case of a chicken are removed from the egg, and tested to ensure that they are not immunoreactive with the uncleaved protein.

The methods of the present invention may be used for diagnosing a disease, disorder, or condition associated with cell apoptosis. Such methods comprise contacting a cell, tissue, group of cells, or samples thereof, with an antibody of the present invention and detecting, or failing to detect, the antibody bound to the neoepitope. Detecting the antibody bound to the neoepitope is indicative of apoptosis, whereas failing to detect the antibody bound to the neoepitope suggests apoptosis is not present in the cell, tissue, group of cells, or samples thereof.

In yet another embodiment, the present invention provides methods of screening compounds to identify inhibitors of apoptosis. These methods comprise exposing a sample of cells to conditions known to activate apoptosis in the cells, contacting the sample with a test or candidate compound, contacting the sample with an antibody of the present invention, and quantifying or detecting the level of antibody bound to the neoepitope in the sample. In preferred embodiments, a second sample is induced into apoptosis and is subjected to the same steps as the first sample except the second sample is not contacted with the test compound. The use of the untreated (by the test compound) second sample allows one to compare the level of antibody bound to the neoepitope in cells treated with the test compound, versus antibody levels in cells not treated with the test compound. The test compound is said to inhibit apoptosis if the level of the antibody in the first sample is less than the level of the antibody in the second sample.

In another embodiment, the present invention provides methods for screening compounds to identify stimulators or inducers of apoptosis. Such methods comprise contacting a sample of cells with a test compound, contacting the sample with an antibody of the present invention, and quantifying or detecting the level of antibody bound to the neoepitope in the sample. In preferred embodiments, a second sample is subjected to the same steps as the first sample except the second sample is not contacted with the test compound. The use of the untreated second sample allows one to compare the level of antibody bound to the neoepitope in cells treated with the test compound versus cells not treated with the test compound. The test compound induces apoptosis if the level of the antibody in the first sample is greater than the level of the antibody in the second sample.

Also provided by the present invention are kits for detecting apoptosis. Specifically, the kits are for detecting apoptosis-generated protein fragments in a sample. Such kits comprise an antibody of the present invention. In some embodiments, the antibody of the present invention comprises a label. In other embodiments, the antibody of the present invention is not labeled, but the kit further comprises a labeled secondary antibody that is immunoreactive with the antibody of the present invention.

Other reagents that the kits of the present invention optionally comprise antibodies immunoreactive with surface antigens (such as CD4, CD8, TCR, B220, Fas), antibodies immunoreactive with a proliferation or other marker antigens (such as p21, p53, Rb, PCNA, Ki-67, etc.), or reagents for the TUNEL (TdT-mediated dUTP Nick-End Labeling) reaction (Promega Corporation, Cat. No. #G3250, G7360).

Also provided, are methods of producing an antibody immunoreactive with a neoepitope comprising the amino terminus produced by cleavage of a protein by a protease during apoptosis, but not immunoreactive with the uncleaved protein. Such methods comprise obtaining a polypeptide comprising the amino terminus produced by cleavage of a protein by a protease during apoptosis, administering the polypeptide to an animal to elicit antibody production against the polypeptide, and collecting the antibodies from the animal by methods known to those of skill in the art.

As used herein, "a" and "an" are defined to mean one or more.

BRIEF DESCRIPTION OF THE DRAWINGS

FIG. 1 shows the amino acid sequence of a polypeptide, identified herein as SEQ ID NO:2, used to elicit antibodies specific to the neoepitope of PARP, as illustrated in Example 1.

FIG. 2 identified as SEQ ID NO:5 shows the amino acid sequence from amino acid position 196 to amino acid position 244 of the human poly ADP-ribose polymerase protein (GenPept Acc. No. P09874). The caspase recognition site (DEVD) is shown in bold type, followed by a vertical line showing the site where caspase cleaves the protein. The first seven amino acids of the newly created amino terminus of the resulting about 85 kd fragment produced from the cleavage of PARP with caspase are underlined to show the sequence of the 7-mer polypeptide (SEQ ID NO:2) used in the production of antibodies specific to the terminus of the fragment, as illustrated in Examples 1 and 2.

DETAILED DESCRIPTION OF THE INVENTION

Figure 3:
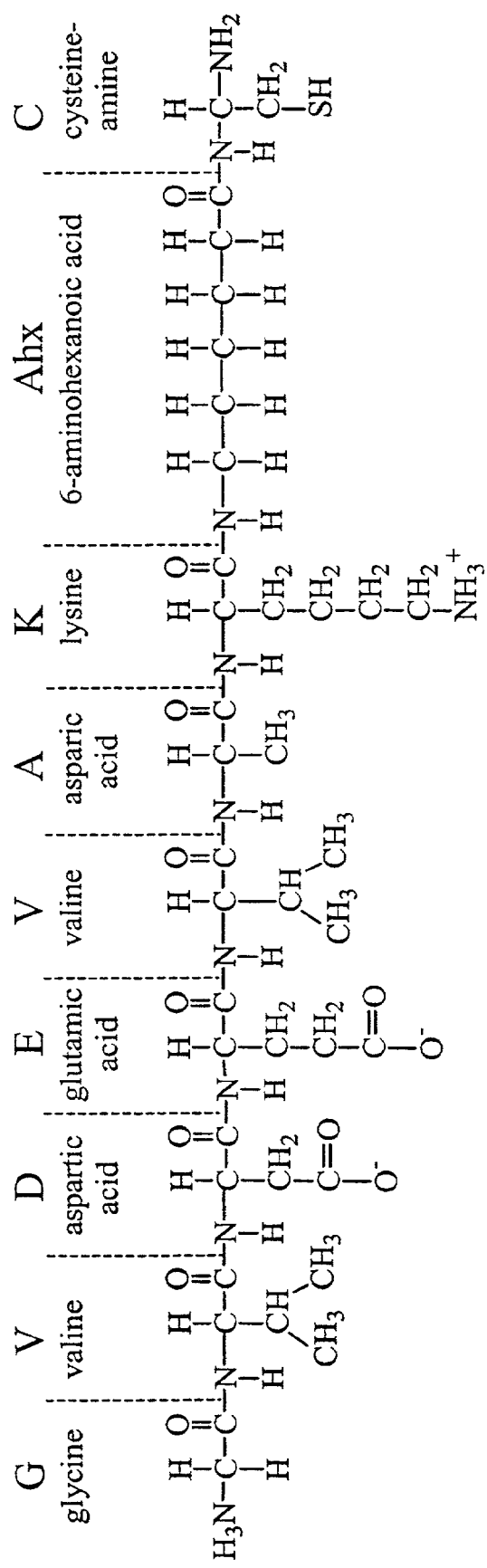
FIG. 3 presents, in diagrammatic form, a structure of the polypeptide and linker molecule used in Example 1 to produce antibodies of the present invention.

The present invention provides compositions comprising antibodies that are immunoreactive with (i.e., specific to) neoepitopes produced in apoptotic cells. Because an integral step of apoptosis is specific cleavage of specific cellular proteins by caspases, the new amino terminus that results from such cleavage provides an excellent antigen for the production of apoptosis-specific antibodies. Antibodies of the present invention, raised to a new amino terminus which results from cleavage specific to apoptosis, such as antibodies raised to the new amino terminus of the about 85 kd fragment resulting from cleavage of PARP after cleavage with caspase, are immunoreactive with the new amino terminus produced by cleavage of the protein by a caspase during apoptosis. Importantly, the antibodies are not immunoreactive with the non-cleaved protein. Embodiments of the present invention include the antibodies themselves and antibodies with equivalent function, methods of making the antibodies, methods of using the antibodies, and kits that contain the antibodies.

A. Caspases and Proteolytic Substrates

1. Proteases and Proteolytic Substrates During Apoptosis

Poly-ADP-ribose polymerase (PARP) is one of a number of proteins whose proteolytic degradation is stimulated in cells undergoing apoptosis. Other such proteins include Keratin 18 (K18) (Caulin et al., *J. Cell. Biol.*, 138(6): 1379–94, 1997), MEKK-1 (Cardone et al., *Cell*, 90(2): 315–23, 1997), DNA replication complex C, DNA-dependent protein kinase, protein kinase of presenilin 1 and 2, and spectrin (fodrin). These proteins are cleaved during apoptosis by a family of proteases known as caspases. A review of caspases and their protein targets is provided by Nicholson and Thornberry, *TIBS*, 22(8):299–306 (1997).

The caspases recognize and cleave immediately after a distinct sequence of amino acids within a protein. Based on knowledge of the recognition site of caspase 3 (CPP32), the cleavage site and subsequent new amino terminus of the protein fragment corresponding to the carboxyl portion of PARP is predicted. A similar method may be used to predict the new amino terminus of other proteins cleaved by the caspases as well. A list of such proteins is shown in Table 1. It is contemplated that, given the methods disclosed herein, antibodies specific to the newly formed amino terminus formed by caspase cleavage may be produced for any of these proteins. Such antibodies are likely to be apoptosis-specific antibodies, which are readily determined by methods disclosed herein.

As provided herein, one would locate the caspase cleavage site within the amino acid sequence of the protein, produce a polypeptide that comprises the new amino terminus formed by cleavage of a caspase, immunize an animal with the polypeptide, collect the antibodies from the animal, and screen the antibodies for the ability to recognize the cleaved form of the protein and not the uncleaved form of the protein. When the animal is a bird, such as a chicken, the antibodies are preferably collected from a bird egg. Of course, one may chose not to screen the antibodies, but it is preferred that one screens the antibodies to insure that they are specific to the new amino terminus.

Embodiments of the present invention include antibodies to the new amino terminus of PARP produced by cleavage of PARP by a caspase during apoptosis. Because this amino terminus is not present in uncleaved PARP, the antibodies are specific to a PARP fragment produced during apoptosis. To produce the antibodies, a polypeptide comprising the new amino terminus of PARP are administered to animals in a manner compatible with eliciting an immune response and production of antibodies within the animals. It is contemplated that the antibody could also be produced by injecting chickens and recovering antibodies from the eggs. In a preferred embodiment, the polypeptide is GVDEVAK (SEQ ID NO:2, illustrated in FIG. 1). In a more preferred embodiment, this polypeptide further comprises the chemical structure illustrated in FIG. 3. It is preferred that the compound of FIG. 3 is conjugated to a carrier protein to increase its immunogenicity.

TABLE 1

Proteolytic substrates for caspases during apoptosis

| Site[a] | Cleaved protein | Reference |
| --- | --- | --- |
| DEVD G | PARP | Kaufmann, S. H. et al. (1993) |
|  |  | Lazebnik, et al. (1994) |

TABLE 1-continued

Proteolytic substrates for caspases during apoptosis

| Site[a] | Cleaved protein | Reference |
| --- | --- | --- |
| DEVD N | DNA-PKcs | Casciola-Rosen, L. A. et al. (1995, 1996) |
|  |  | Teraoka, H. et al. (1996) |
|  |  | Le Romancer, M. et al. (1996) |
|  |  | Song, Q. et al. (1996) |
| DGPD G | U1-70K snRNP | Casciola-Rosen, L. A. et al. (1994) |
| DXXD X | HnRNP-C | Waterhouse, N. et al. (1996) |
| DEPD S | SREBP (+) | Wang, X. et al. (1995, 1996) |
| DELD S | D4-GDI | Na, S. et al. (1996) |
| DXXD X | Huntingtin | Goldberg, Y. P. et al. (1996) |
| DETD S | DFF-45 site I (+) | Liu, X. et al. (1997) |
| DAVD T | DFF-45 site II (+) | Liu, X. et al. (1997) |
| DEVD G | DNA-RC C140 | Ubeda, M. and Habener et al. (1997) |
|  |  | Song, Q. et al. (1997) |
| DMQD N | PKC δ (+) | Emoto, Y. et al. (1995) |
|  |  | Gayhur, T. et al. (1996) |
| DSID S | Rb | An, B. and Dou, Q. (1996) |
|  |  | Jänicke, R. U. et al. (1996) |
|  |  | Chen, W-D. et al. (1997) |
|  |  | Tan, X. et al. (1997) |
| DVPD C | HDM2/MDM2 | Chen, L. et al. (1996) |
| DQTD S | FAK | Crouch, D. H. et al. (1996) |
| DSLD L | NuMA | Hsu, H-L. et al. (1996) |
|  |  | Casiano, C. A. et al. (1996) |
| XXXD X | Pro-caspase (+) |  |
| DMQD N | α-Fodrin | Martin, S. et al. (1995) |
|  |  | Vanags, D. M. et al. (1996) |
|  |  | Cryns, V. L. et al. (1996) |
| ELPD G | Actin | Mashima, T. et al. (1995, 1997) |
|  |  | Chen, Z. et al. (1996) |
|  |  | Song, Q. et al. (1997) |
|  |  | Brown, S. B., et al. (1997) |
| SRVD G | Gas2 | Broncolini, C., et al. (1995) |
| VEID N | Lamins | Lazebnik, Y. A. et al. (1995) |
| $P_4P_1$ |  | Orth, K. et al. (1996) |
|  |  | Takahashi, A. et al. (1996) |
|  |  | Rao, L. et al. (1996) |

[a]Cleavage sites, indicated with the space, have been determined by protein sequencing or mutational analysis (except for NuMA and α-fodrin, which are sites corresponding to the molecular mass of cleavage products). (Nicholson and Thornberry, TIBS, 22 (8):299–306, 1997)

The first thirty amino acids of the new amino terminus of the polypeptide formed by the cleavage of human PARP during apoptosis is identified herein as SEQ ID NO:1. The antibody of the present invention is preferably raised to a polypeptide with a sequence of amino acids beginning with at least three of the first amino acids at the amino terminus of SEQ ID NO:1, including but not limited to a 6-mer polypeptide identified by SEQ ID NO:3 and a 9-mer polypeptide identified by SEQ ID NO:4. The polypeptide of FIG. 1, consisting of an amino acid sequence identified by the first 7 amino acids, i.e. SEQ ID NO:2, from the new amino terminus of PARP in humans is preferred for use in the production of antibodies of the present invention. However, other polypeptides comprising the new amino terminus of PARP are suitable. Two criteria should be considered when choosing polypeptides for the production of antibodies to the new amino terminus of PARP: (1) the amino terminus of the polypeptide should resemble that of the new amino terminus of the about 89 kd of PARP formed by cleavage during apoptosis as closely as possible (i.e., should be glycine or structures chemically resembling glycine) and (2) the longer the polypeptide, the more likely it will assume a structure similar to uncleaved PARP. Given the above factors, it is preferred that the polypeptide used in the present invention comprise 3 to 25 amino acids, more preferably 5 to 15 amino acids, and even more preferably about 5 to about 10 amino acids and most preferably 7.

Because the antibodies raised to the new amino terminus of human PARP are able to recognize the new amino terminus of PARP of non-human species, antibodies raised to polypeptides comprising the new amino terminus of the PARP of other species may be cross-reactive with human PARP. The caspase cleavage site of PARP of several species is shown in Table 2.

TABLE 2

| Species (GenPept Acc. No.) | Site | New Amino Terminus |
|---|---|---|
| Human (P09874) | D E V D | G V D E V A K |
| Rat (P27008) | D E V D | G I D E V A K |
| Mouse (P11103) | D E V D | G T D E V A K |
| Bovine (P18493) | D E V D | G I D E V T K |
| Chicken (P26446) | E E V D | G N V V A T K |
| Xenopus (P31669) | D E V D | G H S A A G K |

The antibodies of the present invention may be used in methods of detecting and measuring apoptotic proteolysis, in methods of identifying and quantifying cells undergoing apoptosis in vitro and in vivo, and methods of identifying compounds that stimulate or block apoptosis.

The methods of the invention may be used to diagnose a disease, disorder, or condition which is of either pathological or non-pathological origin including chronic neurodegenerative diseases (such as Alzheimer's disease), cancer, sepsis, trauma, hypoxia, anoxia, ischemia (such as ischaemic reperfusion injury), spinal trauma, head trauma, lesion, rheumatoid arthritis, viral infections (such as EBV and HIV) and exposure to toxins.

In another embodiment, the present invention provides methods of identifying compounds that are useful in inhibiting or inducing apoptosis. Such methods may be in vitro, in vivo, or ex vivo.

In a preferred embodiment, the present invention provides immunoassays for detecting the result of proteolytic activity associated with apoptosis. Such immunoassays include, but are not limited to, Western blots, ELISA, cell-based ELISA, filter-binding ELISA, inhibition ELISA, sandwich ELISA, immunostaining, immunoprecipitations, slot or dot blots, radioimmunoassays, scintillation proximity assays, Ouchterlony analysis, and fluorescent immunoassays (including flow cytometry) using antibodies conjugates or antigen conjugates of fluorescent substances such as fluorescein, rhodamine, or phycoerythrin.

2. Methods for Preparing Antibody Compositions

The antibody compositions of the present invention may be produced by a number of methods Means for preparing and characterizing antibodies are well known in the art (See e.g., Harlow, E. and Lane, D., *Antibodies: A Laboratory Manual*, Cold Spring Harbor Laboratory, Cold Spring Harbor, N.Y., 1988). Reference to antibodies throughout the specification includes whole polyclonal and monoclonal antibodies ("mAbs"), and parts thereof, either alone or conjugated with other moieties. Antibody parts include Fab and F(ab)$_2$ fragmented and single chain antibodies. The antibodies may be made in vivo in suitable laboratory animals or in vitro using recombinant DNA techniques (e.g., U.S. Pat. Nos. 4,975,369 and 5,225,539).

Briefly, a polyclonal antibody of the present invention is prepared by immunizing an animal with an immunogen comprising the new amino terminus of proteins cleaved during apoptosis and collecting antisera from that immunized animal. A wide range of animal species can be used for the production of antisera. Typically an animal used for production of antisera is a sheep, a donkey, a chicken, a rabbit, a mouse, a rat, a hamster, a goat, or a guinea pig. Because of the relatively large blood volume of rabbits, a rabbit is a preferred choice for production of polyclonal antibodies.

As is well known in the art, a given composition may vary in its immunogenicity. It is often necessary therefore to boost the host immune system, as may be achieved by coupling a peptide or polypeptide immunogen to a carrier. Exemplary and preferred carriers are keyhole limpet hemocyanin ("KLH") and bovine serum albumin ("BSA"). Other albumins such as ovalbumin, mouse serum albumin or rabbit serum albumin can also be used as carriers. Means for conjugating a polypeptide to a carrier protein are well known in the art and include glutaraldehyde, m-maleimido-benzoyl-N-hydroxysuccinimide ester ("MBS"), carbodiimide and bis-diazotized benzidine.

Antibodies, both polyclonal and monoclonal, specific for epitopes comprising the new amino terminus of proteins cleaved during apoptosis may be prepared using immunization techniques, as are generally known to those of skill in the art. A composition containing antigenic epitopes of the polypeptide of interest is used to immunize one or more experimental animals, such as a rabbit or mouse, which will then proceed to produce specific antibodies against the polypeptide. Polyclonal antisera may be obtained, after allowing time for antibody generation, by bleeding the animal and preparing serum samples from the whole blood, or in the case of chickens, by purifying the antibody from the eggs.

In preferred embodiments, the antibodies of the present invention are further purified by a process known as affinity purification. Methods of affinity purification of antisera, or other antibody compositions, are well known to those of skill in the art. Generally, an antibody composition is subjected to chromatography wherein the antigen is coupled to the resin of a column. Antibodies that are immunoreactive with the antigen are retained in the column, whereas antibodies (and other proteins) that are not immunoreactive with the antigen flow through. The immunoreactive antibodies are then eluted from the column. Elution may be by a number of methods. One such method includes the addition of 100% ethylene glycol to the column (Fornstedt, *FEBS Lett.*, 177:195–199, 1984), while another is demonstrated in Example 1 herein.

The amount of immunogen composition used in the production of polyclonal antibodies varies upon the nature of the immunogen, as well as the animal used for immunization. A variety of routes can be used to administer the immunogen (subcutaneous, intramuscular, intradermal, intravenous and intraperitoneal). The production of polyclonal antibodies may be monitored by sampling blood of the immunized animal at various points following immunization. A second, booster injection, also may be given. The process of boosting and titering is repeated until a suitable titer is achieved. When a desired level of immuneogenicity is obtained, the immunized animal can be bled and the serum isolated and stored, and/or the animal can be used to generate mAbs. One of the aspects of the present invention is a polyclonal sera that is relatively homogenous with respect to the specificity of the antibodies therein. Typically, polyclonal antisera is derived from a variety of different "clones." i.e., B cells of different lineage; mAbs, by contrast, are defined as coming from antibody-producing cells with a common B-cell ancestor, hence their "mono" clonality.

mAbs may be readily prepared through use of techniques such as those exemplified in U.S. Pat. No. 4,196,265.

Typically, the production of mAbs involves immunizing a suitable animal with a selected immunogen composition, e.g., a purified or partially purified protein, polypeptide or peptide. The immunization composition is administered in a manner effective to stimulate antibody producing cells. Rodents such as mice and rats are preferred animals, however, the use of rabbit, sheep or frog cells is also possible. The use of rats may provide certain advantages (Goding, "Monoclonal Antibodies: Principles and Practice," 2$^{nd}$ Edition, Academic Press, Orlando, Fla., pp. 60–74, 1986), but mice are preferred, with the BALB/c mouse being most preferred as this is most routinely used and generally gives a higher percentage of stable fusions.

Following immunization, somatic cells with the potential for producing antibodies, specifically B lymphocytes (B cells), are selected for use in the mAb generating protocol. These cells may be obtained from biopsied spleens, tonsils or lymph nodes, or from a peripheral blood sample. Spleen cells and peripheral blood cells are preferred, the former because they are a rich source of antibody-producing cells that are in the dividing plasmablast stage, and the latter because peripheral blood is easily accessible. Often, a panel of animals will have been immunized and the spleen of animal with the highest antibody titer will be removed and the spleen lymphocytes obtained by homogenizing the spleen with a syringe. Typically, a spleen from an immunized mouse contains approximately about $5 \times 10^7$ to about $2 \times 10^8$ lymphocytes.

The antibody-producing B lymphocytes from the immunized animal are then fused with cells of an immortal myeloma cell line, generally one of the same species as the animal that was immunized. Myeloma cell lines suited for use in hybridoma-producing fusion procedures preferably are non-antibody producing, have high fusion efficiency, and enzyme deficiencies that render them incapable of growing in certain selective media which support the growth of only the desired fused cells (hybridomas).

Any one of a number of myeloma cell lines may be used, as are known to those of skill in the art (Goding, "Monoclonal Antibodies: Principles and Practice," 2$^{nd}$ Edition, Academic Press, Orlando, Fla., pp. 60–74, 1986; Campbell, "Monoclonal Antibody Technology, Laboratory Techniques I Biochemistry and Molecular Biology," Burden and Von Knippenberg, Eds., Elsevier, Amsterdam, 13:75–83, 1984). For example, where the immunized animal is a mouse, one may use P3-X63/Ag8, X63-Ag8, 653, NS1/1, Ag4 1, Sp210-Ag14, FO, NSO/U, MPC-11, MPC11-X45-GTG 1.7 and S194/5XX0 Bul. For rats, one may use R210.RCY3, Y3-Ag 1.2.3, IR983F and 4B210. U-266, GM1500-GRG2, LICR-LON-HMy2 and UC729–6 are all useful in connection with human cell fusions.

One preferred murine myeloma cell is the NS-1 myeloma cell line (also termed P3-NS-1-Ag4-1), which is readily available from the NIGMS Human Genetic Mutant Cell Repository by requesting cell line repository number GM3573. Another mouse myeloma cell line that may be used is the 8-azaguanine-resistant mouse murine myeloma SP2/O non-producer cell line.

Methods for generating hybrids of antibody-producing spleen or lymph node cells and myeloma cells usually comprise mixing somatic cells with myeloma cells in a 2:1 ratio, though the ratio may vary from about 20:1 to about 1:1, respectively, in the presence of an agent or agents (chemical or electrical) that promote the fusion of cell membranes. Fusion methods using Sendai virus have been described (Kohler and Milstein, Nature, 256:495–497, 1975; Eur. J. Immunoi., 6:511–519, 1976), and those using polyethylene glycol (PEG), such as 37% (v/v) PEG, by Gefter et al., Somatic Cell Genet., 3(2):231–236 (1977). The use of electrically induced fusion methods is also appropriate (Goding, "Monoclonal Antibodies: Principles and Practice," 2$^{nd}$ Edition, Academic Press, Orlando, Fla., pp. 60–74, 1986).

Fusion procedures usually produce viable hybrids at low frequencies, about $1 \times 10^{-6}$ to about $1 \times 10^{-8}$. However, this does not pose a problem, as the viable, fused hybrids are differentiated from the parental, unfused cells (particularly the unfused myeloma cells that would normally continue to divide indefinitely) by culturing in a selective medium. The selective medium is generally one that contains an agent that blocks the de novo synthesis of nucleotides in the tissue culture medium. Exemplary and preferred agents are aminopterin, methotrexate, and azaserine. Aminopterin and methotrexate block de novo synthesis of both purines and pyrimidines, whereas azaserine blocks only purine synthesis. Where aminopterin or methotrexate is used, the medium is supplemented with hypoxanthine and thymidine as a source of nucleotides (HAT medium). See, e.g., Current Protocols in Immunology, eds. J. E. Coligan, et al, John Wiley and Sons, Inc. 1992. Where azaserine is used, the medium is supplemented with hypoxanthine.

The preferred selection medium is HAT. Only cells capable of operating nucleotide salvage pathways are able to survive in HAT medium. The myeloma cells are defective in key enzymes of the salvage pathway, e.g., hypoxanthine phosphoribosyl transferase (HPRT), and they cannot survive. The B-cells can operate this pathway, but they have a limited life span in culture and generally die within about two weeks. Therefore, the only cells that can survive in the selective medium are those hybrids formed from myeloma and B-cells.

This culturing provides a population of hybridomas from which specific hybridomas are selected. Typically, selection of hybridomas is performed by culturing the cells by single-clone dilution in microtiter plates, followed by testing the individual clonal supernatants (after about two or three weeks) for the desired reactivity. The assay should be sensitive, simple and rapid, such as radioimmunoassays, enzyme immunoassays, cytotoxicity assays, plaque assays, dot immunobinding assays, and the like.

The selected hybridomas would then be serially diluted and cloned into individual antibody-producing cell lines. The clones can then be propagated indefinitely to provide mAbs. The cell lines can be exploited for mAb production in two basic ways. A sample of the hybridoma can be injected (often into the peritoneal cavity) into a histocompatible animal of the type that was used to provide the somatic and myeloma cells for the original fusion. The injected animal develops tumors secreting the specific mAb produced by the fused cell hybrid. The body fluids of the animal, such as serum or ascites fluid, can then be tapped to provide mAbs in high concentration. The individual cell lines could also be cultured in vitro, where the mAbs are naturally secreted into the culture medium from which they can be readily obtained in high concentrations. mAbs produced by either means may be further purified, if desired, using filtration, centrifugation and various chromatographic methods such as HPLC or affinity chromatography.

3. Polypeptides Used to Generate Desired Antibodies

Polypeptides are disclosed herein as amino acid residue sequences. Those sequences are written left to right in the direction from the amino to the carboxy terminus. In accordance with standard nomenclature, amino acid residue sequences are denominated by either a single letter or a three-letter code as indicated in Table 3 below.

TABLE 3

| Amino Acid Residue | 3-Letter Code | 1-Letter Code |
|---|---|---|
| Alanine | Ala | A |
| Arginine | Arg | R |
| Asparagine | Asn | N |
| Aspartic Acid | Asp | D |
| Cysteine | Cys | C |
| Glutamine | Gln | Q |
| Glutamic Acid | Glu | E |
| Glycine | Gly | G |
| Histidine | His | H |
| Isoleucine | Ile | I |
| Leucine | Leu | L |
| Lysine | Lys | K |
| Methionine | Met | M |
| Phenylalanine | Phe | F |
| Proline | Pro | P |
| Serine | Ser | S |
| Threonine | Thr | T |
| Trytophan | Trp | W |
| Tyrosine | Tyr | Y |
| Valine | Val | V |

Modifications and changes can be made in the structure of a polypeptide of the present invention and still obtain a molecule having like characteristics and function. For example, certain amino acids can be substituted for other amino acids in a sequence without appreciable loss of receptor activity. Because it is the interactive capacity and nature of a polypeptide that defines that polypeptide's biological functional activity, certain amino acid sequence substitutions can be made in a polypeptide sequence (or, of course, its underlying DNA coding sequence) and nevertheless obtain a polypeptide with like properties.

In making such changes, the hydropathic index of amino acids can be considered. The importance of the hydropathic amino acid index in conferring interactive biologic function on a polypeptide is generally understood in the art (Kyte and Doolittle, *J. Mol. Biol.*, 157:105–132, 1982). It is known that certain amino acids can be substituted for other amino acids having a similar hydropathic index or score and still result in a polypeptide with similar biological activity. Each amino acid has been assigned a hydropathic index on the basis of its hydrophobicity and charge characteristics. Those indices are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−0.3); proline (−1.6); histidine (−3.2); glummate (−3.5); asparatate (−3.5); asparagine (−3.5); lysine (−3.9); and arginine (−4.5).

It is believed that the relative hydropathic character of the amino acid determines the secondary structure of the resultant polypeptide, which in turn defines that interaction of the polypeptide with other molecules, such as enzymes, substrates, receptors, antibodies, antigens, and the like. It is known in the art that an amino acid can be substituted by another amino acid having a similar hydropathic index and still obtain a functionally equivalent polypeptide. In such changes, the substitution of amino acids whose hydropathic indices are within +/−2 is preferred, those which are within +/−1 are particularly preferred, and those within +/−0.5 are even more particularly preferred.

Substitution of like amino acids can also be made on the basis of hydrophilicity, particularly where the biological functional equivalent polypeptide or peptide thereby created is intended for use in immunological embodiments. U.S. Pat. No. 4,554,101, incorporated herein by reference, states that the greatest local average hydrophilicity of a polypeptide, as governed by the hydrophilicity of its adjacent amino acids, correlates with its immunogenicity and antigenicity, i.e. with a biological property of the polypeptide.

As detailed in U.S. Pat. No. 4,554,101, the following hydrophilicity values have been assigned to amino acid residues: arginine (+3.0); lysine (+3.0); aspartate (+3.0 +/−1); glutamate (+3.0+/−1); serine (+0.3); asparagine (+0.2); glutamine (+0.2); glycine (0); proline (−0.5 +/−1); threonine (−0.4); alanine (−0.5); histidine (−0.5); cysteine (−1.0); methionine (−1.3); valine (−1.5); leucine (−1.8); isoleucine (−1.8); tyrosine (−2.3); phenylalanine (−2.5); tryptophan (−3.4). It is understood that an amino acid can be substituted for another having a similar hydrophilicity value and still obtain a biologically equivalent, and in particular, an immunologically equivalent polypeptide. In such changes, the substitution of amino acids whose hydrophilicity values are within +/−2 is preferred, those which are with in +/−1 are particularly preferred, and those within +/−0.5 are even more particularly preferred.

As outlined above, amino acid substitution are generally therefore based on the relative similarity of the amino acid side-chain substituents, for example, their hydrophobicity, hydrophilicity, charge, size, and the like. Exemplary substitutions which take various of the foregoing characteristics into consideration are well known to those of skill in the art and include: arginine and lysine; glutamate and aspartate; serine and threonine; glutamine and asparagine; and valine, leucine and isoleucine (See Table 4, below). The present invention thus contemplates functional or biological equivalents of a polypeptide comprising the new amino terminus of a protein cleaved by a caspase during apoptosis.

TABLE 4

| Original Residue | Exemplary Substitutions |
|---|---|
| Ala | Gly; Ser |
| Arg | Lys |
| Asn | Gln; His |
| Asp | Glu |
| Cys | Ser |
| Gln | Asn |
| Glu | Asp |
| Gly | Ala |
| His | Asn; Gln |
| Ile | Leu; Val |
| Leu | Ile; Val |
| Lys | Arg |
| Met | Met; Leu; Tyr |
| Ser | Thr |
| Thr | Ser |
| Trp | Tyr |
| Tyr | Trp; Phe |
| Val | Ile; Leu |

4. Immunochemical Methods

The antibodies of the present invention will have particular use as reagents in immunochemical methods. Immunochemical methods include, but are not limited to, Western blotting, immunoaffinity purification, immunoprecipitation, ELISA, dot or slot blotting, RIA, immunohistochemical staining, immunocytochemical staining, and flow cytometry.

a. Flow Cytometry

The antibodies of the present invention may be used in methods of flow cytometry. Methods of performing flow cytometry to detect apoptosis are discussed in Zhang et al., *The Journal of Immunology*, 157:3980–3987 (1996) and Pepper et al., *Leuk. Res.*, 22(5):439–444 (1998). Generally, the cells are permeabilized to allow the antibody to enter and exit the cell. After permeabilization, the cells are incubated with an antibody. In preferred embodiments, the antibody is a monoclonal antibody. It is more preferred that the monoclonal antibody be labeled with a fluorescent marker. If the antibody is not labeled with a fluorescent marker, a second antibody that is immunoreactive with the first antibody and contains a fluorescent marker is used. After sufficient washing to insure that excess or non-bound antibodies are removed, the cells are ready for flow cytometry. Of course, the staining technique described above is also appropriate for the preparation of cells for other methods (e.g., fluorescent microscopy).

Using the antibodies of the present invention for flow cytometry, apoptotic cells would be indicated by an increase in the fluorescent intensity of the cell over control, non-apoptotic cells. The apoptotic cells may be sorted by their increase in fluorescence and subjected to further analysis (Zhang et al., *The Journal of Immunology*, 157:3980–3987, 1996).

b. Immunoassays

Immunoassays of the invention include the various types of enzyme linked immunosorbent assays (ELISAs), as are known to those of skill in the art. However, it will be readily appreciated that other useful embodiments include radioimmunoassays ("RIAs") and other non-enzyme linked antibody binding assays and procedures.

U.S. Pat. No. 5,744,319 describes the use of antibodies to human tryptase in what is commonly known as a double antibody-sandwich ELISA. The basic protocol for a double antibody-sandwich ELISA is as follows: A plate is coated with antibodies (called capture antibodies) specific for the antigen being assayed. The plate is then washed with a blocking agent, such as bovine serum albumin (BSA) to block non-specific binding of proteins (antibodies or antigens) to the test plate. The test sample is then incubated on the plate coated with the capture antibodies. The plate is then washed, incubated with detect antibodies, washed again, and incubated with a specific antibody-label conjugate. After incubation, the unbound conjugate is washed from the plate. The presence of the bound antibody-label conjugate is indicated by detection of the label.

In preferred embodiments, the capture antibody is an anti-PARP antibody (i.e. to the about 89 kd fragment of PARP) of the present invention and the detect antibody is an antibody that is immunoreactive with the region of PARP corresponding to the carboxy terminal fragment of caspase-cleaved PARP but is not specific to the new amino terminus (such as clone C2–10, Pharmingen; San Diego, Calif.; Cat. #65196E). Of course, in light of the present disclosure many variations of a double antibody-sandwich ELISA will be apparent to those of skill in the art, including using the anti-PARP antibody of the present invention as the detecting antibody or the detecting antibody may be labeled.

In other ELISAs, proteins or peptides are immobilized onto a selected surface, preferably a surface exhibiting a protein affinity, such as the wells of a polystyrene microtiter plate. After washing to remove incompletely adsorbed material, one would then generally desire to bind or coat a nonspecific protein that is known to be antigenically neutral with regard to the antibodies of the present invention, such as bovine serum albumin (BSA) or casein, onto the well. This allows for blocking of nonspecific adsorption sites on the immobilizing surface and thus reduces the background caused by nonspecific binding of antibodies onto the surface. When the antibodies were created in an animal by conjugating a polypeptide to a carrier protein (e.g., KLH), it is preferred that a protein different from the carrier protein be used as a blocking agent, because of the possibility of the presence of antibodies to the blocking protein in the antibody composition.

After binding of antigenic material to the well, coating with a non-reactive material to reduce background, and washing to remove unbound material, the immobilizing surface is contacted with an antibody composition of the present invention in a manner conducive to immune complex (antigen/antibody) formation. Such conditions preferably include diluting the antibody composition of the present invention with diluents such as BSA, bovine gamma globulin (BGG) and phosphate buffered saline (PBS)/Tween® 20. These added agents also tend to assist in the reduction of nonspecific background. The layered antibody composition is then allowed to incubate for, e.g., from 2 to 4 h, at temperatures preferably on the order of about 25° C. to about 37° C. Following incubation, the antibody composition-contacted surface is washed so as to remove non-immunocomplexed material. A preferred washing procedure includes washing with a solution such as PBS/Tween® 20, or borate buffer.

Following formation of specific immunocomplexes between the test sample and the antibody composition of the present invention, and subsequent washing, the occurrence and the amount of immunocomplex formation may be determined by subjecting the complex to a second antibody having specificity for the antibody of the present invention. To provide a detecting means, the second antibody will preferably have an associated detectable label, such as an enzyme label or fluorescent molecule that will generate a signal, such as color development upon incubating with an appropriate substrate. Thus, for example, one will desire to contact and incubate the antibody-bound surface with a peroxidase-conjugated anti-rabbit IgG for a period of time and under conditions that favor the development of immunocomplex formation (e.g., incubation for 2 h at room temperature in a PBS-containing solution such as PBS/Tween® 20). The second antibody also may be conjugated to a hapten such as biotin that can be detected by avidin or streptavidin conjugated to an associated, detectable label.

After incubation with the second enzyme-tagged antibody, and subsequent to washing to remove unbound material, the amount of label is quantified by incubation with a chromogenic substrate such as urea and bromocresol purple or 2.2'-azino-di-(3-ethylbenzthiazoline)-6 sulfonic acid ("ABTS") and $H_2O_2$, in the case of peroxidase as the enzyme label. Quantitation is then achieved by measuring the degree of color generation, e.g., using a visible spectrum spectrophotometer.

A number of immunoassays are discussed in U.S. Pat. Nos. 5,736,348, 5,192,660, and 4,474,892.

c. Western Blots

The compositions of the present invention will find use in immunoblot or Western blot analysis. Methods of Western blotting are well known to those of skill in the art and detailed methods are provided in the Current Protocols in Immunology (Id.). Generally, a protein sample is subjected to SDS-PAGE at such conditions as to yield an appropriate separation of proteins within the sample. The proteins are then transferred to a membrane (e.g., nitrocellulose, nylon, etc.) in such a way as to maintain the relative positions of the proteins to each other.

In preferred embodiments, visibly labeled proteins of known molecular weight are included within a lane of the gel. These proteins serve as a method of insuring that adequate transfer of the proteins to the membrane has occurred and as molecular weight markers for determining the relative molecular weight of other proteins on the blot.

Subsequent to transfer of the proteins to the membrane, the membrane is submersed in a blocking solution to prevent nonspecific binding of the primary antibody. In preferred embodiments, the primary antibody is an antibody to the new amino terminus of proteins cleaved during apoptosis. In more preferred embodiments, the antibody recognizes the new amino terminus created by the cleavage of PARP by caspase 3 or caspase 7 during apoptosis.

The primary antibody may be labeled and the presence and molecular weight of the antigen may be determined by detection of the label at a specific location on the membrane. However, in preferred embodiments, the primary antibody is not labeled and the blot is further reacted with a labeled secondary antibody. This secondary antibody is immunoreactive with the primary antibody. In preferred embodiments, the secondary antibody is antibody to rabbit immunoglobulins and labeled with alkaline phosphatase (Promega, Madison, Wis.; Cat. #5373B) or horseradish peroxidase.

An apparatus for, and methods of performing, Western blots are described in U.S. Pat. No. 5,567,595.

d. Immunoprecipitation

The antibodies of the present invention are particularly useful for the isolation of antigens by immunoprecipitation. Methods of immunoprecipitations are described in U.S. Pat. No. 5,629,197. Immunoprecipitation involves the separation of the target antigen component from a complex mixture, and is used to discriminate or isolate minute amounts of protein. For the isolation of cell-surface localized proteins, nonionic salts are preferred, since other agents, such as bile salts, precipitate at acid pH or in the presence of bivalent cations.

5. Screening Assays

In yet another aspect, the present invention contemplates a process of screening substances for their ability to affect apoptosis. Utilizing the methods and compositions of the present invention, screening assays for the testing of candidate substances can be derived. A candidate substance is a substance which potentially can promote or inhibit apoptosis within a cell sample contacted with the substance.

A screening assay of the present invention generally involves determining the ability of a candidate substance to affect cellular processes leading to the production of an epitope that is immunoreactive with an antibody composition of the present invention.

As is well known in the art, a screening assay provides a cell, or group of cells, under conditions suitable for testing apoptosis. These conditions include pH, temperature, tonicity, and the presence of relevant factors involved in apoptosis (e.g., growth factors).

The pH is preferably from about a value of 6.0 to a value of about 8.0, more preferably from a value of about 6.8 to a value of about 7.8 and, most preferably a value of about 7.4. In a preferred embodiment, temperature is from about 20° C. to about 50° C., more preferably from about 30° C. to about 40° C. and, even more preferably about 37° C. Osmolarity is preferably from about 5 milliosmolar to about 400 milliosmolar and, more preferably from about 200 milliosmolar to about 400 milliosmolar and, even more preferably from about 290 milliosmolar to about 310 milliosmolar. The presence of factors can be required for the proper testing of apoptosis in specific cells. Such factors include, for example, the presence or absence (withdrawal) of a growth factor, cytokine, such as an interleukin, colony stimulating factors, or neurotrophic factor.

a. Screening Assays for Compounds that Induce Apoptosis

The present invention provides a process of determining the presence of an epitope produced in cells that are undergoing apoptosis, thus a method of detecting apoptosis. Therefore, such a method may be utilized to determine if a candidate substance is inducing apoptosis in a biological sample. A biological sample to be screened can be a biological fluid such as extracellular or intracellular fluid or a cell or tissue extract or homogenate. A biological sample can also be an isolated cell (e.g., in culture) or a collection of cells such as in a tissue sample or histology sample. A tissue sample can be suspended in a liquid medium or fixed onto a solid support such as a microscope slide.

In accordance with a screening assay process, a biological sample is exposed to a candidate compound being assayed. Typically, exposure is accomplished by contacting the biological sample with the candidate compound. Of course, one may contact a large number of cells with the candidate compound and a biological sample may be taken from those cells. For example, one may administer the candidate compound to an animal and collect a biological sample from the animal. Administration may be orally, transdermally, superficially, by inhalation, vaginally, retroductally (such as intraductal in mammary gland), intraveneously, intranasally, subcutaneously, rectally, or intermuscularly. Methods of administering compositions to animals by these routes are well known to those of skill in the art.

The biological sample may be a blood sample or a tissue sample. The tissue sample may be a biopsy, wherein the animal may not need to be sacrificed prior to collection of the sample, or may be a tissue sample collected from an animal following euthanasia or a sample collected during autopsy.

The biological sample is exposed to the candidate compound under conditions and for a period of time sufficient for induction of apoptotic processes. Such conditions and time periods may be determined by using compounds known to induce apoptosis in a given sample. Biological reaction conditions include ionic composition and concentration, temperature, pH and the like. Ionic composition and concentration can range from that of distilled water to a 2 osmolar solution. Preferably, osmolarity is from about 100 milliosmolar to about 400 milliosmolar and, more preferably from about 200 milliosmolar to about 300 milliosmolar. Temperature preferably is from about 4° C. to about 100° C., more preferably from about 15° C. to about 50° C. and, even more preferably from about 25° C. to about 40° C. pH is preferably from about a value of 4.0 to a value of about 9.0, more preferably from about a value of 6.5 to a value of about 8.5 and, even more preferably from about a value of 7.0 to a value of about 7.5. The only limit on biological reaction conditions is that the conditions do not cause a significant level of apoptosis in the absence of a candidate compound but do allow apoptosis in the presence of a known inducer of apoptosis.

Exposure time will vary inter alia with the biological conditions used, the concentration of compound and the nature of the sample (e.g., fluid or tissue sample). Means for determining exposure time are well known to one of ordinary skill in the art. Typically, where the sample is fluid, the exposure time is from about 10 minutes to about 200 minutes, although longer exposure times may be needed in some techniques (e.g., neuronal growth factor (NGF) withdrawal). The presence of apoptosis in the sample is detected by contacting the sample with the apoptosis specific antibodies of the present invention and detecting the formation and presence of antibody-polypeptide conjugates. Means for detecting such antibody-antigen conjugates are disclosed herein. In one embodiment, detection is accomplished by detecting an indicator affixed to the antibody. Exemplary and well known such indicators include radioactive labels (e.g., $^{32}$P, $^{125}$I, $^{14}$C), fluorescent labels, such as fluoroscein, rhodamine, or phycoerythrin, a second antibody or an enzyme such as horseradish peroxidase, alkaline phosphatase, or luciferase. Means for affixing indicators to antibodies are well known in the art. Commercial kits are available for the purpose.

b. Screening Assay for Compounds that Inhibit Apoptosis

Similar to the above assay for screening compounds for their ability to induce apoptosis, the present invention also provides methods for screening compounds that inhibit apoptosis. Generally, such methods involve subjecting a biological sample to conditions that induce apoptosis. These conditions may be conditions commonly known to induce apoptosis or may be conditions found to induce apoptosis by methods described herein. Such conditions include, but are not limited to, pH, temperature, tonicity, the presence of relevant factors involved in apoptosis (e.g., growth factors), or compounds capable of inducing apoptosis (e.g., anisomycin, etoposide, dexamethasone, valinomycin, merocyanine 540, or butyrate).

It is contemplated that the cells could be contacted with a candidate compound suspected to inhibit apoptosis prior to, simultaneous with, or following induction of apoptosis in the biological sample. In preferred embodiments of this screening assay, the cells are contacted with the candidate compound following induction of apoptosis, and then screened as follows:.

First, the biological sample is exposed to the candidate compound for a period of time sufficient for inhibition of apoptotic processes. Such time periods may be determined by using compounds known to inhibit apoptosis in a given sample. Exposure time will vary inter alia with the biological conditions used, the concentration of compound and the nature of the sample (e.g., fluid or tissue sample). Means for determining exposure time are well known to one of ordinary skill in the art. Typically, where the sample is fluid, the exposure time is from about 10 minutes to about 200 minutes.

Then, the presence of apoptosis in the sample is detected by contacting the sample with the apoptosis specific antibodies of the present invention and detecting the formation and presence of antibody-polypeptide conjugates. Means for detecting such antibody-antigen conjugates are disclosed herein. In one embodiment, detection is accomplished by detecting an indicator affixed to the antibody. Exemplary and well known such indicators include radioactive labels (e.g., $^{32}$P, $^{125}$I, $^{14}$C), fluorescent labels, such as fluoroscein, rhodamine, or phycoerythrin, a second antibody or an enzyme such as horseradish peroxidase, alkaline phosphatase, or luciferase. Means for affixing indicators to antibodies are well known in the art. Commercial kits are available.

The ability to inhibit apoptosis is indicated by a reduced level of antibody-polypeptide conjugates in the sample as compared to a sample, subjected to the same conditions and inducer of apoptosis as the test sample, that was not contacted with the candidate compound.

6. Kits

In another aspect, the present invention provides for kits for detecting the presence of epitopes that are immunoreactive with the antibodies of the present invention. Such kits comprise a first container containing a first antibody being an antibody of the present invention, with the antibody present in an amount sufficient to perform at least one assay. In a preferred embodiment, the first antibody is immunoreactive with the new amino terminus produced by cleavage of PARP by a caspase during apoptosis.

The assay kits of the invention may further comprise a second container containing a second antibody that immunoreacts with the first antibody. Preferably, the secondary antibody is conjugated with a label (enzymatic, fluorometric, radioactive, etc.). The secondary antibody may be from essentially any animal including, but not limited to cow, goat, sheep, horse, rabbit, chicken, or donkey. In some preferred embodiments, the secondary antibody is a goat antibody that is imunoreactive with rabbit antibodies.

In another embodiment, the kit of the present invention may further comprise an antibody recognizing a proliferation marker (such as anti-PCNA or anti-Ki-67). Such kits would have particular utility in techniques for determining the status of a tumor sample. In another embodiment, the kits of the present invention further comprise an antibody to a surface marker (such as antibodies to the CD antigens). Such kits would have particular utility in flow cytometry techniques allowing one to determine the type of cells undergoing apoptosis in a mixture of cell types.

In a preferred embodiment, the kits of the present invention further comprise other antibodies or reagents for detecting apoptosis. Other antibodies and reagents for detecting apoptosis include, but are not limited to, reagents for performing the TUNEL reaction (such as the reagents of the Apoptosis Detection System, Fluorescein and colorimetric; Promega; Madison, Wis.; Cat. #G3250, G7360), Annexin V (Gatti et al., *J. Histochem. Cytochem.*, 46(8):895–900, 1998), calcein (Gatti et al., *J. Histochem. Cytochem.*, 46(8): 895–900, 1998), and CaspACE™ reagents (Promega; Madison, Wis.; Cat. #G3540, G3751, G720). Such kits may contain a separate container means for each antibody or reagent or may optionally combine two or more reagents in one container means. Of course, when combining reagents, it is important that the combination not affect the activity of either reagent, and it is preferred that the combination is such that the ratio of the reagents is useful in its intended assay.

In other embodiments, the kits of the present invention may include compositions known to induce apoptosis such as anisomycin, etoposide, dexamethasone, valinomycin, merocyanine 540, or butyrate.

EXAMPLES

The following examples are included for illustrative purposes. It will be appreciated by those of skill in the art that the techniques disclosed in the examples which follow represent techniques that function well in the practice of the invention, and thus can be considered to relate to preferred modes for its practice. However, those of skill in the art should, in light of the present disclosure, appreciate that many changes can be made in the specific embodiments which are disclosed and still obtain a like or similar result without departing from the spirit and scope of the invention.

PARP is an enzyme involved in DNA repair that is cleaved by caspase activity during the process of apoptosis (Kaufmann et al., *Cancer Research*, 53:3976–3985, 01993).

PARP is an about 116 kd polypeptide present in about 106 copies per somatic cell. Caspase cleavage of PARP (as well as other caspase substrates) results in the generation of a newly-formed unique amino terminus in apoptotic cells that normally would not be present in non-apoptotic cells.

Caspase cleavage of PARP occurs at the carboxyl terminal side of the aspartate residue of the DEVD caspase recognition sequence between Asp 214 and Gly 215 of PARP. This area of PARP is shown in FIG. 2. Caspase cleavage separates the amino terminal nick sensor region from the carboxyl terminal catalytic domain. The cleavage results in an about 30 kd amino terminal DNA binding domain and a about 85 kd carboxyl terminal domain with basal PARP activity.

In Examples 1 and 6, below, antibodies to the new amino terminus created by the cleavage of PARP during apoptosis were produced, using polypeptides with amino acid sequences identical to the first sequence of amino acids at the amino terminus of SEQ ID NO:1. The polypeptide used in example 1 is a 7-mer, identified as SEQ ID NO:2. Two different polypeptides were used in Example 6, a 6-mer, identified as SEQ ID NO:3, and a 9-mer, identified as SEQ ID NO:4. The Examples below also illustrate methods of isolating and using the antibodies of the invention to detect apoptosis in a variety of different samples.

Example 1

Production of Antibodies to the New Amino Terminus Created by Cleavage of PARP During Apoptosis, Using a 7-mer Polypeptide A. Synthesis of 7-Mer Polypeptide and Conjugation to KLH To create antibodies to the new amino terminus of PARP created by caspase cleavage, a seven amino acid polypeptide corresponding to the amino terminal seven amino acids of the 85 kd PARP fragment (underlined amino acids in FIG. 2 SEQ. ID NO:2) was synthesized and linked to a six carbon spacer arm and a C-terminal cysteine-amide to yield the molecule of FIG. 3.

The molecule of FIG. 3 was conjugated, through the carboxy-terminal cysteine residue of the molecule to Keyhole Limpet Hemocyanin ("KLH"), a carrier protein. Prior to conjugation, KLH was activated by the following procedure:
1. 350 mg of KLH was dissolved in 30 ml of $H_2O$.
2. 70 mg of MBS was dissolved in no more than 3 ml of dimethyl formamide ("DMF").
3. The MBS solution was mixed with the KLH solution, and stirred for 30 min.
4. 10% the resulting mixture was dialyzed in $H_2O$, to determine exact yield, and analyzed as follows:
   a. The dialyzed material was dried down.
   b. The mass of dialyzed material was measured, and multiplied by 10 to obtain the mass of the whole. The mass of dialyzed material was subtracted from whole mass to determine the mass of the remaining 90%.
5. The remaining 90% of the mixture was dialyzed in Phosphate-Buffered Saline ("PBS"). This dialyzed material was aliquotted into 4 mg samples based on the following calculation:

$$\frac{\text{Fraction Weight}}{\text{Fraction Volume}} = \frac{4 \text{ mg}}{x \text{ ml}}$$

6. 4 mg aliquots were lyophilized and frozen until needed.
7. When needed, a 4 mg aliquot of lyophilized sample was solubilized. 4 mg of polypeptide was added, and the aliquot shaken for 2 hours.

B. Production of Antisera to the 7-mer Polypeptide

The resulting KLH-conjugated polypeptide was used to produce antisera to the polypeptide in rabbits. Injection and recovery of antisera was performed as follows:
1. A rabbit was initially immunized with 400 μg of KLH-conjugated polypeptide suspended in Freunds Complete adjuvant
2. The rabbit was injected with a booster shot of 200 μg of KLH-conjugated polypeptide suspended in Freunds Incomplete adjuvant 12 weeks after the initial immunization
3. Antiserum was collected using two separate bleedings of the rabbit. One bleeding was 10 days after the boost. The other bleeding was 13 days after the boost.

C. Purification of Antibodies from the Antiserum

Following collection, the antisera were combined and affinity purified, according to the following procedure:
1. Coupling to Gel
   a) Polypeptides and Sulfolink® gel (Pierce; Rockford, Ill.; Cat. #20401.) were allowed to come to room temperature.
   b) A Tris/EDTA (50 mM Tris, 5 mM EDTA-Na, pH 8.5) buffer was prepared.
   c) Disposable chromatography columns were each packed with an appropriate amount of Sulfolink® gel (about 2 ml of gel per each column).
   d) Each column was equilibrated with 10 volumes of the Tris/EDTA buffer.
   e) Caps on the top and bottom of each column were replaced.
   f) 1 mg of polypeptide per 1 ml of gel in was dissolved in the Tris/EDTA buffer and added to the gel in each column. (i.e., about 2 mg of polypeptide per column).
   g) The gel and solution were mixed well, so that the bed of each column became unpacked. The gel and solution were mixed on a shaker for 15 minutes, being careful not to shake so vigorously that the beds would break.
   h) The columns were allowed to incubate at room temperature for 30 minutes.
   i) The buffer was drained from each column and washed with 10 volumes of Tris/EDTA buffer.
2. Blocking Non-Specific Sites on Gel
   j) Caps on the top and bottom of each column were replaced.
   k) 1 ml of blocking buffer (50 mM cysteine solution in 50 mM Tris, 5 mM EDTA-Na, pH 8.5) per 1 ml of gel (usually 2 ml of buffer) was added to each column.
   l) The gel and solution were mixed so that the bed of each column became unpacked. The columns were shaken on a shaker for 15 minutes, taking care not to shake so vigorously that the beads would break.
   m) The columns were allowed to incubate at room temperature for 30 minutes.

n) The buffer was drained from each column, and the column washed with 20 volumes of salt buffer (1 M NaCl).
o) The caps were replaced on the top and bottom of column. Azide buffer was added to any column to be stored for later use, and the column was refrigerated in an upright position.

3. Antibody Binding p) Each column was washed with 10 column volumes of phosphate buffer.
q) Up to 47 ml of serum was mixed with the gel in a 50 mL conical container.
r) The conical container was incubated at 4° C. in a styrofoam cooler overnight on a shaker.

4. Elution of Antibody s) The gel and serum were poured back into the column. The flow-through was collected in a separate container, labeled, and stored in a cold room (4° C.) for later use.
t) The remaining gel and serum were washed with 25 column volumes of salt buffer (about 0.5 M NaCl) to remove non-specific antibody.
u) The antibody was eluted from each column with glycine buffer. 15–20 ml was collected in a 50 ml conical container, containing 1.1 ml Tris-HCL pH 9.5. This is enough base to neutralize the 15–10 mL sample.
v) The eluted antibody was dialyzed in dialysis buffer (10 mM sodium phosphate, 20 mM sodium chloride, pH 7.4) overnight with 1 change before the end of the day.
w) The dialyzed antibody was frozen until needed.
x) The column was stored by adding azide buffer thereto, and refrigerating upright.

Example 2

Specific Recognition of the New Amino Terminus Created by Cleavage of PARP During Apoptosis The antibodies generated in Example 1 were used in a Western blot procedure to demonstrate their ability to recognize the about 85 kd fragment of PARP and their inability to recognize uncleaved PARP.

A. Materials and Methods

1. Cleavage of PARP

Bovine spleen PARP (0.22 mg/ml; BIOMOL, Plymouth Meeting, Pa.; Cat #SE-165) was cleaved with recombinant CPP32 (Pharmingen International, San Diego, Calif.; Cat #66281T). In a tube, 104 µl of cleavage buffer (20 mM PIPES, 100 mM NaCl, 10 mM DTT, 1 mM EDTA, 0.1% CHAPS, 10% sucrose) (pH 7.2) were combined with 91 µl (20 µg) bovine spleen PARP, and 5 µl (1 µg) of recombinant CPP32. For efficient cleavage of PARP by CPP32, the tube was incubated at 37° C. for two hours. The reaction was stopped by transferring to −20° C. Uncleaved PARP was obtained directly from the stock tube for Western analysis.

2. Induction of Apoptosis in HL-60 Cells

Human promyelomonocytic leukemia cells, HL-60, were cultured in RPMI-1640 (Sigma; St. Louis, Mo.) and 10% fetal bovine serum (Hyclone) using standard tissue culture protocol. Log phase HL-60 cells were pelleted (350 g for 5 min) and resuspended in fresh medium at $5 \times 10^5$ cells/ml.

Apoptosis was induced in an aliquot of the cells by incubation in the presence of anisomycin (2 µg/ml) (Sigma) for 2 hours at 37° C. To be used as a control for cells that were not induced into apoptosis, a separate aliquot was incubated for 2 hours at 37° C. in the absence of anisomycin. After the incubation period, the treated and untreated cells were pelleted as before and washed twice with ice cold phosphate buffered saline (PBS). Subsequently, the cells were resuspended in 1 ml PBS and transferred to a microcentrifuge tube, pelleted and resuspended in PBS and 4× sample buffer (2.0 ml glycerol, 2.0 ml 10% SDS, 0.25 mg bromphenol blue, 2.5 ml stacking gel 4× buffer (6.06 g Tris-Base, 4 ml 10% SDS, adjusted to pH 6.8 with concentrated HCl and brought to 100 ml with $H_2O$, 4% DTT, $H_2O$ to 10 ml) to a concentration of $4 \times 10^5$ cells/20 µl. The samples (lysates) were then heated to 97° C. for 5 min and stored at −20° C. until use.

3. Western Blot

Aliquots containing 125 ng of PARP from Tube A (full length PARP) and from Tube B (PARP cleaved by recombinant caspase 3) were combined with 4× sample buffer (see above). The aliquots and the lysates from treated and untreated HL-60 cells were heated for 3 min at 97° C. Samples were then vortexed and centrifuged at 4000×g for 1 min. Samples were loaded on to a 4–20% SDS-PAGE pre-cast gel (Novex, San Diego, Calif.; Cat #EC60252) and the gel was run at constant current (30 mAmps) for 1 hr at room temperature. The gel buffer was Laemmli buffer (25 mM Tris-base and 192 mM glycine)+0.1% SDS.

The contents of the gel were then transferred to a nitrocellulose filter using the BIORAD trans-blot system (Cat #162-0115). The transfer was performed at 100 V for 1 hr at 4° C. in 20% methanol in Laemmli buffer (25 mM Tris-base, 192 mM glycine). Transfer was confirmed by Coomassie blue staining of the gel followed by destaining in 50% methanol/10% glacial acetic acid. Following transfer, the filter was stained with 0.2% Ponceau S to visualize the individual lanes. The filter was then cut to allow incubation with different antibodies.

Prior to incubation with the 1° Abs, the filters were blocked with TBST (20 mM Tris-HCL pH 7.6; 150 mM NaCl; and 0.05% (v/v) Tween-20) plus 1% bovine serum albumin (Bayer, Fraction V; Cat #81-003-3) overnight at 4° C. The primary antibody (1:1000 dilution) was incubated with the filters for 2 hr at RT with oscillation. After the incubation period, the filters were washed three times with oscillation for 15 min in TBST. Subsequently, the filters were incubated with the 2° Ab (donkey anti-rabbit AP; Jackson Laboratories, West Grove, Pa.; Cat. #711-055-152; 0.6 mg/ml stock used at 1:5000 dilution) for 1 hr at room temperature with oscillation, followed by washing the filters three times for 10 min in TBST then washing in TBS (20 mM Tris-HCl, pH 7.6; 150 mM NaCl).

To visualize the antibody-antigen complexes, the filters were developed with Western Blue (Promega, Madison, Wis.; Cat #5384B) for 5–10 min in the dark.

B. Specific Recognition of Cleaved PARP

To demonstrate that the antibodies generated in Example 1 were specific to the cleaved form of PARP, the antibodies were used in a Western blot procedure on a gel containing PARP purified from bovine spleen. To create cleaved PARP, the PARP purified from bovine spleen was cleaved with recombinant CPP32. A 1:1000 dilution of the affinity purified antibodies failed to produce a signal in the lane containing uncleaved PARP. However, using these same antibodies, a band was easily visible in the lane containing PARP cleaved with recombinant CPP32. When a 1:2000 dilution of antibodies that recognize both cleaved and uncleaved PARP was used (Boehinger Mannheim, Indianapolis, Ind.; Cat. #1835238), a single band corresponding to uncleaved PARP was visualized in the uncleaved sample, while two bands corresponding to uncleaved and cleaved PARP were visualized in the cleaved sample.

To demonstrate that the antibodies produced by the method of Example 1 were specific to epitopes produced in apoptotic cells, protein lysates were made from HL-60 cells treated with anisomycin to induce apoptosis and untreated HL-60 cells. A 1:1000 dilution of the affinity purified antibodies failed to produce a band in the untreated cell lane when used in a Western blot, but was able to produce a band corresponding in size to the cleaved form of PARP in the treated cells. To ensure the presence of the uncleaved form of PARP in both samples, a 1:2000 dilution of the antibodies that recognize both cleaved and uncleaved PARP was used. Uncleaved PARP was detected in lysates from both the untreated and treated HL-60 cells, whereas the cleaved form is only detected in the sample from the treated cells.

Example 3

Immunohistochemical Analysis of Apoptotic Cells Using Antibodies to the New Amino Terminus Created by Cleavage of PARP During Apoptosis The antibodies produced according to Example 1 were used in immunohistochemical analysis to detect cells undergoing apoptosis.

A. Materials and Methods

1. Generation of HL-60 Apoptotic Cell Smears

HL-60 cells were grown as described in Example 2. When the cells were at a concentration of about $3 \times 10^5$ cells/ml, the cells were pelleted and resuspended in fresh RPMI 1640 with 10% fetal bovine serum at a concentration of $5 \times 10^5$ cells/ml. The cells were then split into two aliquots (3 ml/aliquot). One aliquot, hereafter referred to as the "treated cells", was incubated with anisomycin (2 μg/ml) for 1.5 hr at 37° C. and 5% $CO_2$. The other aliquot, hereafter referred to as the "untreated cells", was incubated for 2.5 hr at 37° C. and 5% $CO_2$ in the absence of anisomycin. After the incubation, the cells were pelleted (5 min, 400×g), washed twice with DPBS (Sigma; St. Louis, Mo.; Cat. #D-8537) and pelleted, and each pellet was resuspended in 5 ml DPBS and 5 ml MonoSol fixative from a MonoPrep 2 starter kit (MonoGen, Inc.; Herndon, Va.: Cat. #SK210). The cells were diluted to $10^5$/ml using 1:1 DPBS and MonoSol and 106 (10 ml) of the cells were added to MonoPrep "collection vials".

The cell preps were processed onto microscope slides using the MonoPrep2 standard slide Preparation Procedure for Monolayer Slide Preparation. Briefly, cells were drawn from the collection vials onto the filters (Ultraclean Filter Assemblies) using the syringe slide filter assembly. The filters were transferred (cell side down) to Fisher Super Frost Plus slides (Fisher Scientific; Pittsburg, Pa.; Cat #12-550-15) using forceps. Five drops of MonoFix reagent were added to the top of each filter for 2 min. Several layers of folded Kimwipe were placed on top of the filters and the cells were transferred to the slides by pressing firmly. The filters were allowed to dry completely for several minutes. The filters were removed with forceps and discarded.

Two of the slides (one control and one anisomycin treated) were fixed for 30 min in 4% paraformaldehyde in a humidified plastic slide rack. The slides were rinsed in DPBS and tranferred to a glass coplin jar containing DPBS and stored at 4° C. Another two slides (one control and one anisomycin treated) were fixed by immersing in acetone for 5 min in a Coplin far. The slides were air dried in a chemical fume hood for 5–10 min then transferred to a Coplin jar containing DPBS and stored at 4° C.

2. Immunohistochemical Staining of HL-60 Cell Smears

The fixed cell smears were treated with 0.3% $H_2O_2$/DPBS for 3 min. The slides were blocked using 5% horse serum in PBS for 15 min, then as much liquid as possible was removed without allowing the slides to dry. Affinity purified anti-PARP fragment antibody was diluted 1:50 in DPBS to a final concentration of 10.88 μg/ml and added to each slide for 45–60 min in a plastic slide rack with humid atmosphere to keep the samples from drying.

Following two 10 min washes with DPBS, a 1:1000 dilution of a biotin conjugated AffiniPurified Donkey Anti-rabbit IgG (H+L) (Jackson laboratories, Inc.; West Grove, Pa.; Cat #711-065-152) was added to each slide for 1 hr. Again the slides were washed twice in DPBS for 10 min each wash.

Horseradish peroxidase conjugated avidin-biotin complex (Vectastain Elite ABC Kit PK6100 Standard; Vector Laboratories; Burlington, Calif.) reagent was prepared by adding 50 μl Reagent A and 50 μl Reagent B to 5 ml DPBS in a dropper bottle. An adequate amount of reagent to cover the cells on the slides was added to each slide and the slides were incubated for 25 min.

Freshly prepared DAB solution (Zymed, South San Francisco, Calif.; BrdU staining Kit; Cat #93-3943) substrate solution was added to the slides for 10 min. DAB substrate solution was prepared by adding 50 μl 20× Buffer concentrate to 950 μl water, then 50 μl $H_2O_2$, then 50 μl DAB were added to the slides.

Following washing twice with DPBS for 10 min, 1–2 drops of glycerol based mounting medium were added on the cells and Corning #1 22×30 mm coverslips were added on top.

B. Immunohistochemical Staining is Selective to Apoptotic Cells

In the paraformaldehyde fixed samples, 63% of anisomycin treated cells were stained with anti-PARP antibodies, whereas only 16% of the untreated cells were stained. In the acetone fixed samples, 72% of the anisomycin treated cells were stained, whereas only 4% of the untreated cells were stained. The stained cells in the untreated samples tended to have an apoptotic (round distinct) morphology and are likely to represent cells undergoing apoptosis in the absence of anisomycin treatment.

Example 4

Comparison of PARP Antibody Staining to Tunel

In order to compare using anti-PARP antibodies to the TUNEL assay to detect apoptotic cells, the TUNEL assay was performed followed by immunocytochemical staining with anti-PARP antibodies on the same HL-60 cell smear.

A. TUNEL Assay

Treated HL-60 cell smears were created as described in Example 3. The cells were permeabilized in 0.2% Triton X-100/PBS for 5 min at room temperature, followed by three, 5 min washes in PBS. The smears were then incubated in equilibation buffer (200 mM potassium cacodylate, pH 6.6; 25 mM Tris-HCl, pH 6.6; 0.2 MM DTT; 0.25 mg/ml BSA; 2.5 mM cobalt chloride) for 5 min at room temperature. TdT mix (50 µl equilibration buffer, 1 µl fluorescein-12-dUTP, and 1 µl of TdT enzyme; Promega; Madison, Wis.; Cat #G3250) is then added to the slides and incubated for 1 hr at 37° C., followed by a rinse in 2×SSC for 15 min at room temperature, and three washes for 5 min in PBS. All subsequent steps were done in the dark to protect the fluorescein signal.

B. Immunocytochemistry

Following the TUNEL assay, the smears were stained with the anti-PARP antibodies. Briefly, the smears were blocked with 1% BSA, 2% horse serum, and 10 µg/ml donkey IgG in PBS, followed by a wash with PBS. The smears were then incubated overnight at 4° C. with a 1:100 dilution (6.7 µg/ml) of affinity purified_anti-PARP antibodies that were preabsorbed with HL-60 cells. The preabsorption was performed by incubating the antibody with lysates of untreated HL-60 cells that were fixed in 10% formalin and rinsed in PBS.

After the overnight incubation, the smears were washed four times with PBS, followed by incubation with 0.3% hydrogen peroxide for 3–5 min at room temperature. The smears were washed three times for 5 min per wash, then incubated for 70 min at room temperature with a 1:500 dilution of donkey anti-rabbit-biotin secondary antibody (Jackson Laboratories; Cat #711-065-152). After three, 5 min washes in PBS, the smears were incubated with 100 µl Streptavidin-HRP (Zymed) for 30 min at room temperature. Following three more washes, DAB reagent (Zymed; Cat #00-2114) was added to the smears. Development was at room temperature for 10 min and was stopped by rinsing with water. Prior to analysis, the smears were mounted in Vectashield.

C. Analysis

Comparison of the same field of cells using fluorescent (TUNEL) and light microscopy allowed comparison of the two techniques. In the treated HL-60 cell sample, approximately 90% (37/41) of the TUNEL positive cells were scored as also staining with the anti-PARP antibody immunocytochemistry procedure. Interestingly, a considerable number of cells in the treated sample were stained by the anti-PARP antibody immunocytochemistry procedure but were negative by the TUNEL assay. This result may be attributed to the ability of the anti-PARP antibody immunocytochemistry procedure to detect an apoptotic step (caspase proteolysis) that is prior to DNA fragmentation. Thus, anti-PARP antibody immunocytochemistry procedure may be a more sensitive method of detecting the early events of apoptosis than the TUNEL assay.

Example 5

Preparation of Antibodies to the New Amino Terminus Created by Cleavage of PARP During Apoptotis, Using a 6-mer Polypeptide and a 9-mer Polypeptide 6-mer and 9-mer polypeptides each having a sequence corresponding to the amino terminal 6 or 9 terminal amino acids of the about 85 kd PARP fragment, shown in FIG. 2), were synthesized and linked to a six carbon spacer arm, a 6-aminohexanoic acid group, and a C-terminal cysteine to yield the two molecules shown below:

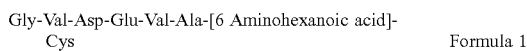
Gly-Val-Asp-Glu-Val-Ala-[6 Aminohexanoic acid]-Cys       Formula 1

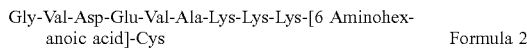
Gly-Val-Asp-Glu-Val-Ala-Lys-Lys-Lys-[6 Aminohexanoic acid]-Cys       Formula 2

The amino acid sequence of the 6-mer polypeptide of Formula 1, i.e. GVDEVA, is identified herein as SEQ ID NO:3. The amino acid sequence of the 9-mer polypeptide of Formula 2, i.e. GVDEVAKKK, is identified herein as SEQ ID NO:4.

The preparation of Formula 1 was determined to be 93% pure by HPLC analysis, and the preparation of Formula 2 was 96% pure. Both preparations were found to be soluble in water. Each polypeptide was conjugated to KLH through the terminal cysteine residue of each formulation, according to the conjugation procedure of Example 1.A. The resulting conjugated polypeptides were used to produce antisera to each polypeptide, in rabbits, according to antibody production procedure of Example 1.B. Specifically, each conjugated polypeptide was injected into a rabbit, the rabbit was boosted two weeks later and the antiserum used in these studies was obtained three weeks after the second boost and stored at 4° C.

Example 6

Purification of Anti-PARP 6-mer and Anti-PARP 9-mer Antibodies from Rabbit Antiserum

A. Preparation of Resins

Three milligrams of the 6-mer and 9-mer polypeptides produced and characterized as described in Example 5, above, were dissolved in separate 3 ml aliquots of TE (50 mM Tris, 5 mM EDTA pH 8.5).

Three milliliters of Sulfolink™ resin (Pierce, 20401) were placed into a 15 ml column for each polypeptide and washed with 30 ml of TE solution. The polypeptides were added to each column and shaken gently, end-over-end, for 15 minutes, then allowed to stand at room temperature for 30 minutes. The columns were then each washed with 30 ml TE solution. Then 3 ml of TE containing 50 mM cysteine (Sigma Corp., C7755) added to each column and the columns were shaken gently, end-over-end, for 15 minutes and allowed to stand at room temperature for 30 minutes. Then each of the columns was washed with 30 ml water and stored overnight at 4° C.

B. Purification of Antibodies

Ten milliliters of rabbit antiserum from rabbits innoculated with the 6-mer polypeptide conjugate prepared as described in Example 5 was added to 10 ml PBS and mixed gently. The resin was then removed from the column and washed with 30 ml PBS, drained, and the resin was added to the serum. The serum/resin mixture was shaken gently, end-over-end, for one hour. The above steps were repeated for the rabbit antiserum from rabbits innoculated with the 9-mer polypeptide prepared as described in Example 5. The serum/resin mixtures were poured into a column and washed with 30 ml PBS until the OD280 of the eluant was less than 0.01. The antibody from each column was eluted with successive 3 ml aliquots of 0.1 M glycine pH 3.1. Affinity purified anti-PARP (9-mer) was collected in five fractions, affinity purified anti-PARP (6-mer) was collected in three fractions. The fraction tubes each contained 0.3 ml 2 M Tris pH 8.0. The fractions for each antibody were pooled and the concentration determined by spectrophotometric reading at OD280. Each antibody was dialyzed against PBS 4° C. The 9-mer polypeptide conjugate yielded 15 ml of 0.327 mg/ml anti-PARP (9-mer) for a total of 4.9 mg. The 6-mer polypeptide conjugate yielded 10 ml of 0.21 mg/ml anti-PARP (6-mer) for a total of 2.1 mg.

Example 7

Immunocytochemistry Analysis of Apoptotic Jurkat Cells Using Affinity Purified Anti-PARP Antibodies Jurkat cells were suspended in fresh medium at a concentration of $5 \times 10^5$ cells per milliliter. Twelve milliliter cultures of the cells were maintained in suspension culture in each of two T-75 flasks. Apoptosis was induced in the cells by treating them with monoclonal anti-Fas antibody (PanVera Corp., SY-001) at a final concentration of 100 ng/ml for 3 hours at 37° C. in 5% $CO_2$. The cells were then harvested by centrifugation at 250×g for 5 minutes. The supernatant was then removed and the cell pellet washed with 7 ml of PBS (Sigma D-8779) and resuspended to $1.5 \times 10^6$ cells per milliliter in PBS.

Poly-1-lysine (Sigma P8920) was diluted in water to 0.1 mg/ml. Then 10 µl of the poly-1-lysine solution was added to each well of an 8 well slide (Cell-Line corporation) and the drop dispersed to cover the entire area of the well. The slides were then air-dried at room temperature for about 45 minutes. The slides were then washed by dipping them several times in water and allowing them to air dry.

The cell suspension was thoroughly mixed and 15 µl added to each well of the slide. The cells were allowed to settle and attach for 5 minutes prior to placing them directly in 10% buffered formalin (Fisher Corp., 23-245684) and incubated at room temperature for 25 minutes. The slides were then washed by dipping them twice in coplain jars containing TBS (Promega Corp., AA640). The cells were then observed to be attached and the slides stored in TBS at 4° C. until used.

The following immunocytochemistry analysis was then performed on three of the apoptosis-induced Jurkat cell slides and three untreated, control, Jurkat cell slides. The six slides were permeabilized by soaking in a coplain jar containing PBS with 0.2% Triton X-100 for five minutes at room temperature. They were then washed three times, five minutes each in a coplain jar containing PBS. They were then blocked for one hour at 37° C. in PBS containing 5% horse serum (Hyclone, SH30074-03) and 0.1% Tween-20 (Sigma, P1379). The primary antibodies (from Example 1) were diluted into the same blocking buffer and about 40 µl added per well. The antibodies and concentrations used are listed below. The slides were then placed horizontally into a humidified chamber and incubated overnight at 4° C.

TABLE 1

| ANTIBODY | FINAL CONCENTRATIONS TESTED |
| --- | --- |
| anti-PARP 6-mer | none, 1.25, 2.5, 5.0 µg/ml |
| anti-PARP 9-mer | none, 1.25, 2.5, 5.0 µg/ml |
| anti-PARP 7-mer | none, 1.25, 2.5, 5.0 µg/ml |

The slides were then washed in a coplain jar four times for 10 minutes each in PBS containing 0.1% Tween-20. This was followed by two washes for 10 minutes each in PBS alone. The slides were drained and 40 µl donkey anti-rabbit Cy3 conjugated antibody (Jackson Labs, #711-165-152, stock 0.625 mg/ml in 50% glycerol), diluted 1:250 in block buffer was added. The slides were incubated, protected from light, for two hours at ambient temperature in a humidified chamber. The slides were then washed twice for 5 minutes each in PBS, once for 5 minutes in PBS containing 0.1% Tween-20, and lastly for 5 minutes in PBS. The wells were mounted using mounting medium containing DAPI (Vector Labs, H1200) and #1 coverslip. The fluorescence was observed with a Zeiss Fluorescent microscope with a 63× objective and rhodamine/DAPI filter cube. Digital photos were taken and analyzed.

The resulting photographs demonstrated all three antibodies tested had preferential reactivity with apoptotic cells. The 7-mer antibody had no background staining on the negative control slides and it also had the strongest apoptosis-specific reactivity. It was optimally reactive at 1.25 µg/ml. The anti-PARP (9-mer) and anti-PARP (6-mer) antibody preparations had low amounts of background reactivity, but did produce faint staining of non-apoptotic cells. Both were optimally reactive at 1.25 µg/ml.

Example 8

Western Blot Analysis Using Anti-PARP (6-mer) and Anti-PARP Anti-PARP (9-mer) Antibodies In this Example the purified antibodies described in Example 6 were used for Western blot analysis. PIPES buffer was prepared to contain the following components: 20 mM PIPES, 100 mM NaCl, 1 mM EDTA, 0.1% CHAPS, 10% sucrose, 70 ml DI water. The buffer was pH adjusted to pH 7.2 and then brought to a final volume of 100 ml with DI water. The buffer was filtered through a 0.2 micron filter and stored sterile at 4° C. DTT was added just prior to use to a final concentration of 10 mM DTT To prepare caspase-3 cleaved PARP antigen, in a 1.5 ml conical tube were combined 2 µg Caspase-3 enzyme (Pharmingen, 66281U), 20 µg uncleaved bovine PARP (Biomol, SE165) and 99 µl PIPES buffer. This will yield 100 µg/ml of PARP at a 10:1 substrate:enzyme ratio. This solution was incubated at 37° C. for two hours with shaking three or four times during this period to keep the reactant suspended. The reaction was stopped by transferring the solution to −20° C.

The samples were prepared to be run on a 4–20% SDS PAGE gel (Novex) as shown in Table 2, below.

TABLE 2

| Sample | ng/well | stock | TBST | 2X Sample Buffer with DTT | load per well |
| --- | --- | --- | --- | --- | --- |
| Uncleaved Bovine PARP | 200 | 4.6 µl | 45 µl | 25 µl | 20 µl |

TABLE 2-continued

| Sample | ng/well | stock | TBST | 2X Sample Buffer with DTT | load per well |
|---|---|---|---|---|---|
| Cleaved PARP | 20 | 1 µl | 49 µl | 50 µl | 20 µl |
| SeeBlue MW Markers | | 20 µl | | | 10 µl |

All the samples were heated at 95° C. for 5 minutes and the gel loaded and run. The proteins run into the gel were then transferred onto nitrocellulose by standard Western blot method. The nitrocellulose membrane was blocked in TBST+1% BSA (Bovine Serum Albumin) at room temperature for one hour. A similar set of the three lanes on the membrane were incubated with each primary anti-PARP antibody preparations (Example 5) diluted 1:5000 in TBST. They were incubated with shaking for one hour at room temperature and then the membranes were washed three times for five minutes each in TBST. Donkey anti-rabbit IgG AP conjugate (Promega Corp.) was diluted 1:5000 in TBST. The membranes were incubated in this secondary antibody for one hour at room temperature and then washed four times in TBST for 5 minutes per wash. The membranes were incubated in Western Blue Stubstrate (Promega Corp.) for up to four minutes to detect the bands.

Both anti-PARP antibodies detected the cleaved PARP on the Western blot with the bands developing on the blot within about two minutes for the anti-PARP (9-mer) antibody and about four minutes for the anti-PARP (6-mer) antibody.

Example 9

Purification of Anti PARP (6-mer) and Anti-PARP (9-mer) Antibodies

This example uses ammonium sulfate precipitation, followed by affinity purification to isolate the anti-PARP (6-mer) and anti-PARP (9-mer) antibodies from rabbit antiserum. Four milliliters of antisera containing antibody specific to the 6-mer polypeptide described in Example 5 were combined with 0.2 ml 5% dextran sulfate (Sigma D5251), and 0.36 ml 1 M $CaCl_2$ (Sigma C3881). The solution was mixed and then incubated at room temperature for 30 minutes. Four milliliters of antisera containing antibody specific to the 9-mer polypeptide described in Example 5 were likewise treated. The solutions were then centrifuged at 14,000 rpm in a microcentrifuge at 4° C. The supernatants were then each brought to 50% saturation with granular ammonium sulfate (Sigma A6387) and incubated overnight at 4° C. The solutions were then transferred to 1.5 ml tubes and centrifuged at 14,000 rpm for 25 minutes at 4° C. The resulting antibody pellets were resuspended in a total of 2 ml TBS for each antibody. Sodium azide was added to a final concentration of 0.02% and the solutions were stored at 4° C. until used.

A. Preparation of Affinity Resin

All reagents were brought to room temperature prior to use. Two milliliters of gel slurry (SuloLink™ resin, Pierce #20401) were placed in a 5 ml polypropylene column (Schleicher & Schuell, 77227). This makes about a 1 ml resin bed when settled. A medium size frit was used on the bottom of the column. The column was allowed to drain by gravity and then equilibrated with 12 ml SulfoLink™ coupling buffer (Pierce, 1852080) in 50 mM Tris pH 8.5, 5 mM EDTA. One milligram of each polypeptide, 6-mer and 9-mer, was added to 2 ml coupling buffer and then each added to a separate 1 ml resin bed. The columns were mixed gently by rocking on a platform rocker for 15 minutes at ambient temperature, protected from the light. They were then incubated stationary for an additional 30 minutes at room temperature. The columns were then drained and washed with 6 ml coupling buffer.

B. Block Column Sites

A 7.9 mg/ml cysteine-HCl (Aldrich, C12,108-0) solution was prepared in coupling buffer. Two milliliters of this solution were added to the resin bed of each of the two columns. The columns were mixed gently by rocking on a platform rocker for 15 minutes at room temperature and then further incubated stationary for 30 minutes at room temperature. The columns were drained and washed with 16 ml of 1 M NaCl, followed by an 8 ml water wash. Sodium azide was added to a final concentration of 0.02% in the final water wash and the columns stored at 4° C.

C. Affinity Purification of Antisera

The resin bed of each column was divided in half and 0.5 ml of the resin bed was used for each purification. All reagents were brought to ambient temperature prior to use. The 0.5 ml resin in the column was washed with 10 ml of TBS by gravity and allowed to drain. The bottom of each column was then sealed. Two ml of the TBS/antisera solution were added to the resin. The caps were added to seal the columns and then they were rocked gently for one hour at ambient temperature. The columns were placed in stands, drained, and each washed with 5 ml TBS. The columns were then each washed with 5 ml TBS/0.5 M NaCl The antibody on each column was eluted into 1.5 ml eppendorf tubes, each containing 20 µl of 2 M Tris pH 8.0 with 4 drops in each fraction (200 µl) of 0.1 M glycine pH3.0 (Sigma G7126). Each fraction was mixed as it was eluted to neutralize it. A total of about 18 fractions were taken. The protein elution was monitored with Pierce Coomassie Plus (Pierce, 18526210) by adding 5 µl sample to 100 µl reagent. They were mixed and the absorbance at 600 nm on a Dynatech MR5000 plate reader was recorded. The fractions with significant absorbance change were pooled for each antibody.

The solutions were then dialyzed using Pierce Slide-A-Lyzer™ 10,000 molecular weight cutoff cassettes (Pierce, 55426) against PBS at 4° C. First one liter of PBS was used for 3 hours, this was then replaced with fresh PBS and the dialysis continued overnight at 4° C. Absorbance readings were taken at 280 nanometers ($A_{280}$) directly, without dilution, on a Beckman DU600 under UV light. Each sample was blanked against PBS. Sodium azide was added to each solution, for a final concentration of 0.02%. The resulting samples were stored at 4° C. until used.

The final yields were 0.44 mg for the anti-PARP (6-mer) antibody and 0.845 mg for the anti-PARP (9-mer) antibody.

Example 10

Immunohistochemistry Analysis Using the Purified Anti-PARP Antibodies

This example compared the antibody preparations purified in Examples 1 and 6 with the antibody preparations purified in Example 9 in an immunohistochemistry application using control and apoptotic, Jurkat cell slides prepared as described in Example 7.

Five slides containing control, untreated Jurkat cells and five slides containing apoptotic Jurkat cells were permeabilized by soaking them in a coplain jar containing PBS+0.2% Triton X-100 (Sigma, T9284) for 5 minutes at room temperature. They were then washed three times for five minutes each in coplain jars containing PBS. They were then blocked in PBS+5% horse serum (Hyclone, SH30074-3) for 90 minutes at 37° C. in a 5% $CO_2$ environment.

Primary antibodies were diluted into blocking buffer as listed in the table below. About 40 μl of each diluted antibody were added to each well. The slides were placed horizontally into a humidified chamber for one hour and then transferred to 4° C. and further incubated overnight.

TABLE 3

| Slide | Antibody | Concentration of Antibodies Used |
|---|---|---|
| 1 | Example 9 anti-PARP (6-mer) | none, 0.1, 0.5, 2.0 μg/ml |
| 2 | Example 9 anti-PARP (9-mer) | none, 0.1, 0.5, 2.0 μg/ml |
| 3 | Example 6 anti-PARP (6-mer) | none, 0.1, 0.5, 2.0 μg/ml |
| 4 | Example 6 anti-PARP (9-mer) | none, 0.1, 0.5, 2.0 μg/ml |
| 5 | Example 1 anti-PARP (7-mer) | none, 1.25, 2.5 μg/ml |

The slides were then washed in coplain jars four times, 10 minutes each, in PBS+0.1% Tween-20. Then followed by two washes, 10 minutes each, in PBS alone. The slides were then drained and the secondary antibody was added. The secondary antibody was Donkey-anti-rabbit, Cy-3 conjugated, diluted 1:250 in blocking buffer (Jackson Immuno. Research Laboratories, Inc., West Grove, Pa., 711-165-152). The slides were then incubated for two hours at room temperature, protected from light. They were then washed in coplain jars protected from light. They were washed twice, 5 minutes each, in PBS, followed by one 5 minute wash in PBS+0.1% Tween-20 and a final 5 minute wash in PBS. The slides were then drained and mounted using mounting medium containing DAPI (35 μl/slide; Vector Labs, H-1 200) and a #1 coverslip.

The fluorescence was observed with a Zeiss, fluorescent microscope, 63× objective. Digital photos were taken with a Diagnostic Spot 2 camera.

While the anti-PARP (9-mer) antibody prepared in Example 6 preferentially reacted with the apoptotic cells, there was high background staining levels in the control cells. Staining with this antibody was optimal at the 0.5 μg/ml concentration. The anti-PARP (9-mer) antibody prepared in Example 9 had little, if any, staining of the control Jurkat cells and intense staining of apoptotic cells at the 0.5 μg/ml concentration. The anti-PARP (6-mer) antibody prepared in Example 9 preferentially reacted with the apoptotic cells and there was minimal staining in the control wells. The anti-PARP (6-mer) antibody prepared in Example 6 resulted in staining of the apoptotic cells, but no staining in the control wells.

The antibody reactive against the 7-mer polypeptide (described in Example 1), provided the most intense signal at the lowest concentration of all the preparations of either of the other two anti-PARP antibodies tested herein (i.e., anti-PARP (6-mer) or anti-PARP (9-mer) antibody). The antibody reaction against the 7-mer consistently provided the most intense signal, and the signal was specific for apoptotic cells with little, if any background signal from staining of the control cells. The optimal concentration for this antibody was 1.25 μg/ml, while the optimal concentration of anti-PARP (6-mer) and anti-PARP (9-mer) antibody preparations was 2.5 μg/ml.

Example 11

Immunocytochemistry Analysis Using Hybridoma Supernatant on Apoptotic Jurkat Cells Hybridoma supernatant was prepared by Harlan Corp. (Madison, Wis.) using the 7-mer polypeptide as described in Example 1. The culture supernatant was contained in DMEM+20% fetal calf serum+HT. For this experiment, undiluted supernatant was used as the source for the dilutions. The Sham medium (no cells) consists of DMEM+20% FCS+HT. The control and anti-Fas antibody induced apoptotic Jurkat cells used in this Example were prepared as described in Example 2 and stored at 4° C. in TBS until used. Three slides of control cells and three slides of apoptotic cells were used. The antibody dilutions used are listed in Table 4, below.

TABLE 4

| | |
|---|---|
| 1. Hybridoma supernatant | none, 1:2, 1:5, 1:15 |
| 2. Sham medium control (negative control) | none, 1:2, 1:5, 1:15 |
| 3. Rabbit anti-PARP antibody (7-mer) (positive control) | none, 1.25 μg/ml, 2.5 μg/ml |

The cells on the slides were permeabilized by soaking the slides in a coplain jar containing PBS+0.2% Triton X-100 for 5 minutes at ambient temperature. The slides were then washed three times, five minutes each, in coplain Jar containing PBS. The slides were blocked using about 35 μl per well of PBS+5% horse serum+0.1% Tween-20. They were blocked in this solution for 90 minutes at 37° C. in a 5% CO2 environment.

The excess was then shaken off and 35 μl of the primary antibody diluted in the blocking buffer as described above, were added per well. The slides were then placed horizontally into a humidified chamber and incubated overnight at 4° C.

The slides were then washed in a coplain jar four times, ten minutes each, in PBS+0.1% Tween-20, followed by two washes, 10 minutes each, in PBS alone. The slides were then dried and 35 μl of the appropriate Cy3 conjugated secondary antibody, diluted 1:250 blocking buffer, were added per well. Donkey-anti-mouse H+L, Cy3, secondary antibody (Jackson Labs, 715-165-150) was used for the slides previously incubated with the hybridoma culture supernatant or the sham medium. Donkey-anti-rabbit H+L, Cy3, secondary antibody (Jackson Labs, 11-165-152) was used for the slides previously incubated with the positive control, rabbit antisera. The slides were then incubated for 2 hours at ambient temperature, protected from the light.

The slides were then washed in a coplain jar protected from light twice, 5 minutes each, in PBS, then 5 minutes PBS+0.1% Tween-20, and a final 5 minute wash with PBS. The slides were then drained and mounted with #1 coverslips using about 35 μl mounting medium which contained DAPI counterstain (Vector Labs, H-1200).

The fluorescence was observed with a Zeiss fluorescent microscope, 63× objective. Digital photos were also taken and analyzed.

The hybridoma supernatant reacted specifically with the apoptotic cells at an optimal dilution of 1:5. The 1.25 µg/ml concentration of the 7-mer antibody reacted specifically with the apoptotic cells and the sham medium control had no resulting fluorescence. The hybridoma supernatant at 1:4 and 1:20 dilution also reacted positively to 100 ng caspase 3-cleaved PARP in a Western blot analysis performed as described in Example 3 with the exception that the secondary antibodies listed above were used at a 1:10,000 dilution.

What is claimed is:

1. A method of detecting apoptosis in a cell or group of cells, said method comprising:
   (a) obtaining a protein sample from a cell or group of cells, wherein the protein sample comprises a neoepitope if apoptosis has been initiated in the cell or group of cells, said amino terminus comprising an amino terminus produced by cleavage of a protein by a caspase during apoptosis;
   (b) contacting said protein with an antibody immunoreactive with the amino terminus, wherein said antibody is not immunoreactive with the protein when not cleaved by the caspase; and
   (c) detecting said antibody bound to the amino terminus, wherein detecting said antibody bound to the amino terminus is indicative of apoptosis in the cell or group of cells.

2. The method of claim 1, wherein the said cell or group of cells is of mammalian origin.

3. The method of claim 2, wherein the said cell or group of cells of mammalian origin is of human origin.

4. The method of claim 3, wherein the human cell or group of cells is a leukemia cell.

5. The method of claim 4, wherein the leukemia cell or group of cells is selected from the group consisting of HL60 and Jurkat cell or cells.

6. The method of claim 1, wherein the antibody is a polyclonal antibody.

7. The method of claim 1, wherein the antibody is a monoclonal antibody.

8. The method of claim 1, wherein the antibody further comprises a label.

9. The method of claim 8, wherein said label is selected from the group consisting of a hapten, an enzyme, a radioactive label, fluorescent label, and a luminescent label.

10. The method of claim 1, wherein the amino terminus comprises a polypeptide with a sequence of amino acids beginning with the at least three of the first amino acids at the amino terminus of SEQ ID NO:1.

11. The method of claim 10, wherein the amino terminus comprises a polypeptide having an amino acid sequence identified by SEQ ID NO:2.

12. The method of claim 10, wherein the amino terminus comprises a polypeptide having an amino acid sequence selected from the group consisting of: SEQ ID NO:3 and SEQ ID NO:4.

13. The method of claim 1, wherein the protein cleaved by the protease during apoptosis is poly(ADP-ribose) polymerase.

14. The method of claim 1, wherein the caspase is selected from the group consisting of caspase 3 and caspase 7.

15. The method of claim 1, wherein detecting said antibody bound to the amino terminus comprises a secondary antibody comprising a label, said secondary antibody recognizing said antibody.

16. A method of detecting apoptosis in cells or tissue, said method comprising:
   (a) obtaining a preparation of cells or tissue, wherein the preparation comprises a neoepitope if apoptosis has been initiated in the cell or tissue, said neoepitope comprising an amino terminus produced by cleavage of a protein by a caspase during apoptosis;
   (b) contacting said cells or tissue with an antibody immunoreactive with the amino terminus, wherein said antibody is not immunoreactive with the protein when not cleaved by the caspase; and
   (c) detecting said antibody bound to the amino terminus, wherein detecting said antibody bound to the amino terminus is indicative of apoptosis in the cell or tissue.

17. The method of claim 1, wherein the protein cleaved by the caspase is selected from the group consisting of Poly-ADP-ribose polymerase, keratin 18, MEKK-1, DNA replication complex C, DNA-dependent protein kinase, protein kinase of presenilin 1 and presenilin 2 and spectrin.

* * * * *

UNITED STATES PATENT AND TRADEMARK OFFICE
CERTIFICATE OF CORRECTION

PATENT NO. : 7,037,664 B2
APPLICATION NO. : 10/011321
DATED : May 2, 2006
INVENTOR(S) : Terry Riss It is certified that error appears in the above-identified patent and that said Letters Patent is hereby corrected as shown below:

*Column 21, line 1, "106" should read --$10^6$--.

Column 21, line 13, "a" should read --an--.

Column 21, line 56, insert --of the-- after "10%" and before "the".

*Column 25, line 56, "106" should read --$10^6$--.

Column 26, line 27, "laboratories" should read --Laboratories--.

*Column 27, line 12, "MM" should read --mM--.

Column 29, line 40, "corporation" should read --Corporation--.

Column 30, line 38, delete the first occurrence of "Anti-PARP".

Column 31, line 25, "Stubstrate" should read --Substrate--.

Column 34, line 39, "CO2" should read --$CO_2$--.

*Column 37, line 7, delete "amino terminus" and insert --neoepitope--.

*Column 37, line 37, delete "with a sequence of amino acids" and insert --having an amino acid sequence--.

*Column 37, line 38, delete "the" between "with" and "at".

UNITED STATES PATENT AND TRADEMARK OFFICE
CERTIFICATE OF CORRECTION

PATENT NO.         : 7,037,664 B2
APPLICATION NO. : 10/011321
DATED                 : May 2, 2006
INVENTOR(S)       : Terry Riss It is certified that error appears in the above-identified patent and that said Letters Patent is hereby corrected as shown below:

*Column 38, line 9, delete "protease" and insert --caspase--.

Signed and Sealed this

Fourteenth Day of November, 2006

JON W. DUDAS
*Director of the United States Patent and Trademark Office*

```
                              SEQUENCE LISTING

<160> NUMBER OF SEQ ID NOS: 5

<210> SEQ ID NO 1
<211> LENGTH: 30
<212> TYPE: PRT
<213> ORGANISM: Homo sapiens

<400> SEQUENCE: 1

Gly Val Asp Glu Val Ala Lys Lys Ser Lys Lys Glu Lys Asp Lys
  1               5                  10                  15

Asp Ser Lys Leu Glu Lys Ala Leu Lys Ala Gln Asn Asp Leu
                 20                  25                  30

<210> SEQ ID NO 2
<211> LENGTH: 7
<212> TYPE: PRT
<213> ORGANISM: Homo sapiens

<400> SEQUENCE: 2

Gly Val Asp Glu Val Ala Lys
  1               5

<210> SEQ ID NO 3
<211> LENGTH: 6
<212> TYPE: PRT
<213> ORGANISM: Homo sapiens

<400> SEQUENCE: 3

Gly Val Asp Glu Val Ala
  1               5

<210> SEQ ID NO 4
<211> LENGTH: 9
<212> TYPE: PRT
<213> ORGANISM: Homo sapiens

<400> SEQUENCE: 4

Gly Val Asp Glu Val Ala Lys Lys Lys
  1               5

<210> SEQ ID NO 5
<211> LENGTH: 49
<212> TYPE: PRT
<213> ORGANISM: Homo sapiens

<400> SEQUENCE: 5

Lys Lys Gln Leu Pro Gly Val Ser Glu Gly Lys Arg Lys Gly Asp
  1               5                  10                  15

Glu Val Asp Gly Val Asp Glu Val Ala Lys Lys Ser Lys Lys Glu
                 20                  25                  30

Lys Asp Lys Asp Ser Lys Leu Glu Lys Ala Leu Lys Ala Gln Asn Asp
                 35                  40                  45

Leu
```